US006274118B1

(12) United States Patent
Diamandis et al.

(10) Patent No.: US 6,274,118 B1
(45) Date of Patent: Aug. 14, 2001

(54) LOCALIZATION AND THERAPY OF NON-PROSTATIC ENDOCRINE CANCER WITH AGENTS DIRECTED AGAINST PROSTATE SPECIFIC ANTIGEN

(75) Inventors: Eleftherios P. Diamandis, Toronto; Russell Redshaw, Nepean, both of (CA)

(73) Assignee: Nordion International Inc. (CA)

( * ) Notice: Subject to any disclaimer, the term of this patent is extended or adjusted under 35 U.S.C. 154(b) by 0 days.

(21) Appl. No.: 09/543,582

(22) Filed: Apr. 5, 2000

Related U.S. Application Data

(62) Division of application No. 08/569,206, filed as application No. PCT/CA94/00392 on Jul. 14, 1994, now Pat. No. 6,068,830.

(30) Foreign Application Priority Data

Jul. 14, 1993 (GB) .................................. 93 14623

(51) Int. Cl.[7] ........................... A61K 51/00; A61M 36/14
(52) U.S. Cl. ................... 424/1.49; 424/1.65; 424/1.69; 424/1.11; 424/9.34; 424/184.1; 424/277.1
(58) Field of Search ................... 424/1.11, 1.49, 424/1.65, 1.69, 9.1, 9.2, 9.3, 9.4, 9.5, 9.6, 9.8, 184.1, 277.1, 9.34

(56) References Cited

U.S. PATENT DOCUMENTS

| 3,927,193 | 12/1975 | Hansen et al. . |
| 4,331,647 | 5/1982 | Goldenberg . |
| 4,348,376 | 9/1982 | Goldenberg . |
| 4,444,744 | 4/1984 | Goldenberg . |
| 4,831,122 | 5/1989 | Buchsbaum et al. . |
| 5,162,504 | 11/1992 | Hjoroszewicz . |
| 5,273,743 | * 12/1993 | Ahlem et al. ........................ 424/85.8 |
| 5,688,658 | * 11/1997 | Diamandis ........................... 435/7.23 |
| 5,723,302 | * 3/1998 | Diamandis ............................. 435/7.1 |
| 6,068,830 | * 5/2000 | Diamandis et al. ................. 424/9.34 |

FOREIGN PATENT DOCUMENTS

| 0217577 | 4/1987 | (EP) . |
| 0453082 | 10/1991 | (EP) . |
| WO 92/01936 | 2/1992 | (EP) . |
| WO 93/01831 | 2/1993 | (EP) . |
| 9502424 | * 1/1995 | (WO) . |

OTHER PUBLICATIONS

Clinical BioChemistry vol. 27, No. 2, (Yu, He et al.), pp. 75–79, dated Apr. 27, 1994.

Database biosis Biosciences Information Service, AN 94:393008.

Bas. Appl. Histochem, vol. 33, No. 1 (Papotti et al.), pp. 25–29 dated 1989.

Journal of Clinical Laboratory Analysis, vol. 8, No. 4, (Yu, He et al.), pp. 251–253, dated 1994.

Michael R. Zalutsky "Antibodies in Radiodiagnosis and Therapy" 1988, pp. 189–235.

Peter K. Leichner "Tumor dosimetry in radioimmunotherapy: Methods for calculation for beta particles" Med. Phys. 20(2), Pt. 2, Mar./Apr. 1993, pp. 529–534.

David M. Goldenberg "Cancer Imaging and Therapy with Radiolabeled Antibodies" Adv. Exp. Med. Biol. 303:107–117.

Peter K. Leichner "An overview of imaging techniques and physical aspects of treatment planning in radioimmunotheapy" Med. Phys. 20 (2), Pt. 2, Mar./Apr. 1993, pp. 569–577.

Zalcberg et al. Tumor Immunotheerapy in Mouse with the Use of[131]I–Labeled Monoclonal Antibodies [1,2], J. Natl. Cancer Inst. No. 3, Mar. 1984, pp. 697–704.

Quadri et al. "Evaluation of Indium–111–and Yttrium–90–Labeled Linker–Immunoconjugates in Nude Mice and Dogs" The Journal of Nuclear Medicine, vol. 34, No. 6, Jun. 1993, pp. 938–945.

Leichner et al. "Patient–Specific Dosimetry of Indium–111–and Yttrium–90–Labeled Monoclonal Antibody CC49" The Journal of Nuclear Medicine, vol. 38, No. 4, Apr. 1997, pp. 512–516.

Erwin et al. "A Radioimmunoimaging and MIRD Dosimetry Treatment Planning Program for Radioimmunotherapy" Nuclear Medicine & Biology, vol. 23, pp. 525–532, 1996.

DeNardo et al. "Prdiction of Radiation Doses from Therapy Uisng Tracer Studies with Iodine–131–Labeled Antibodies" The Journal fo Nuclear Medicine, vol. 37, No. 12, Dec. 1996, pp. 1970–1975.

Mausner et al. "Selection of radionuclides for radioimmunotherapy" Med. Phys. 20 (2), Pt. 2, Mar./Apr. 1993, pp. 503–509.

* cited by examiner

Primary Examiner—Dameron L. Jones
(74) Attorney, Agent, or Firm—Banner & Witcoff, Ltd.

(57) ABSTRACT

It was discovered that prostate-specific antigen is produced by non-prostatic endocrine cancers. It was further discovered that non-prostatic endocrine cancers with steroid receptors can be stimulated with steroids to cause them to produce PSA either initially or at increased levels. This invention relates to the imaging of non-prostatic endocrine cancers by labelled biological binding units which bind to prostate-specific antigen in an imaging procedure, such as, radio imaging or magnetic resonance imaging. Further, the PSA-binding units may be constructed to deliver a toxic agent, such as a radioisotope, toxin or a drug to provide endocrine cancer therapy. Another aspect of the invention is passive immunotherapy against endocrine cancers by treatment with PSA-binding units.

14 Claims, 4 Drawing Sheets

LOCALIZATION AND THERAPY OF NON-PROSTATIC ENDOCRINE CANCER WITH AGENTS DIRECTED AGAINST PROSTATE SPECIFIC ANTIGEN

This application is a divisional of U.S. Ser. No. 08/569,206, filed Apr. 11, 1996, now U.S. Pat. No. 6,068,830, which is a 371 of PCT/CA94/00392, filed Jul. 14, 1994, and claims the benefit of GB 93 14623.1, filed Jul. 14, 1993.

FIELD OF THE INVENTION

This invention relates to the localization and therapy of non-prostatic endocrine cancers by agents that have been constructed to target prostate specific antigen (PSA).

BACKGROUND OF THE INVENTION

Cancer of the breast is the most common cause of cancer death in middle aged women in Europe and North America and both its incidence and mortality are on the increase (1–5). The predominant indications for breast tumor imaging are: detecting the presence of tumor, localizing sites of disease, and following the effects of therapy (6). Trends in scintigraphic imaging have been towards developing imaging pharmaceuticals to provide quantitative information on the pathophysiological characteristics of a tumor, such as its anaplasticity, or likely response to a given therapy (7). For example, to determine via scintigraphic imaging how a patients breast cancer will respond to the administration of a growth suppressor, such as somatostatin, or the estrogen receptor antagonist tamoxifen (8 Diamandis in PCT Application CA 94/00267 has shown that the presence of PSA in breast tumors, as measured by in vitro methods, has prognostic value. Thus, imaging of these tumors may not only reveal occult disease, but may also provide clinically valuable pathophysiological information.

Tumor imaging is commonly carried out using a gamma emitting radionuclide conjugate and a scintillation gamma camera, or with a positron emitting radiopharmaceutical and a positron or PET camera, or with a magneto-pharmaceutical and a magnetic resonance imaging device. The scintillation camera, also known as an Anger camera, consists of a detector head, and a display console. The Anger camera head is composed of sodium iodide crystals that absorb gamma rays and emits the absorbed energy as flashes of light— scintillations that are proportional in brightness to the energy absorbed. In a gamma camera the sodium iodide crystals are coupled to photomultiplier tubes that convert light pulses into electronic pulses. These voltages are translated via a computing circuit to a cathode ray tube. The data from the camera head may be in either analog or digital form that can be stored in a computer and can reconstruct the data to provide an image. Single-photon emission computed tomography (SPECT) imaging involves the use of a gamma scintillation camera where multiple images, typically encompassing 180° or 360°, around the body are taken and the computer issued to reconstruct multiple tomograms in coronal, sagittal, and transverse projections. In PET imaging the positron radionuclide collides with an electron causing annihilation of the particles and creating two photons that travel in 180° opposite directions. The PET system is designed to capture opposite sides and register the count at precisely the same time. A computer is used to manipulate the data and then reconstruct a cross sectional image from this information.

There are a number of approaches to breast tumor imaging that may be divided into two groups: indirect and direct. Indirect techniques, are generally utilized to locate metastatic disease by recognizing the secondary effects of tumor within an organ system. Indirect techniques include, but are not limited to, the use of radiolabelled $^{99m}$Tc phosphonates to locate bone metastases (9,10) and $^{99m}$Tc radiocolloids in liver scans and breast lyphoscintigraphy (11,12,13).

Direct approaches to radionuclide imaging include radiolabelled chemotherapeutic agents, simple ionic substances, metabolite imaging, immunologic and receptor imaging. The use of radiolabelled chemotherapeutic agents, such as bleomycin, have not demonstrated clinical value (14). $^{67}$Ga citrate is the most commonly used simple ionic tracer for tumor imaging, however it localizes in other pathologies and is non specific (15,16,17,18). Metabolite imaging carried out with positron emitting radionuclides such as $^{18}$F-fluorodeoxyglucose, $^{11}$C-methionine and $^{11}$C-thymidine provides tumor metabolism information that has been shown to be clinically valuable for disease staging (19,20,21).

The receptor imaging of breast cancer has been attempted by several approaches. Spicer et al. (22) and Hochberg (23) and others (24–29) have developed radiolabelled estradiols and have been able to demonstrate imaging in estrogen receptor positive breast cancers. It has been postulated that a therapeutic response could result with Auger electrons from $^{123}$I or $^{125}$I radiolabelled estradiols(30,31), or from β emitting radioisotopes such as $^{186}$Re conjugated to progesterone (32). A problem with receptor based imaging is the interference that estrogen receptor antagonists, such as tamoxifen, may have in the clinical environment.

It is known that proteins, such as antibodies, can be developed against specific antigens that are either produced or associated with tumors, can be used to localize tumors. U.S. Pat. No. 3,927,193 to Hansen et al. (33) discloses a process whereby antibodies to carcinoembryonic antigen (CEA) and labelled with $^{125}$I and $^{131}$I were used to image the location of tumors present in hamsters. From this work it was proposed that the location of a tumor in a human could be determined by in vivo administration of a parenteral solution containing an antibody-radioisotope conjugate followed by imaging by a gamma camera. Goldenberg et al. reported success in clinical trials of tumor detection and localization by scintillation scanning of patients that received radiolabelled antibodies to CEA (34).

Based on the original work of Milstein and Kohler (35), monoclonal antibodies have been developed against a variety of tumour antigens such as CA 19.9, CA 125, melanoma associated antigens, TAG 72, fetal protein, ferritin, choriogonadotropin, prostatic acid phosphatase, and PSA for radioimmunoimaging and therapy.

Several investigators have reported on the development of monoclonal antibodies against epitopes of various malignant prostate cell components (36,37,38,39,40). Moreover, PSA was purified and well characterized and found to have a molecular weight in the range of 34,000 (41). PSA is used widely as a tumor marker for in vitro based analyses for diagnostic and monitoring purposes of prostatic carcinoma. U.S. Pat. No. 5,162,504 describes monoclonal antibodies that have been developed to recognize malignant prostate epithelium. These antibodies were developed as diagnostic and prognostic tools for the detection of cancer of the prostate, not as embodied in this invention, for the detection of cancers not associated with the prostate. Until the discovery reported by Diamandis in International Application PCT CA94/00267, it was thought that PSA only occurred in men and was only produced by prostate tissue.

To image breast tumors researchers have developed antibodies directed against TAG 72, CA-3, CEA, EGF-R, LASA-P, and other glycoproteins associated with breast cancer (42,43,44). Khaw et al. developed the monoclonal antibody 323/A3 against a 43 Kd membrane associated glycoprotein from the MCF-7 tumor cell line that was able to image tumors as small as 0.19 grams (45). Rainsbury et al. developed the antibody LICRCON-M8 against human milk fat globule and were also able to demonstrate imaging of human breast tumors, of particular note metastases to the bone were found (46).

Antibodies have been labelled directly with radioisotopes such as $^{123}$I, $^{125}$I, $^{131}$I, $^{18}$F, $^{186}$Re, $^{188}$Re, and $^{99m}$Tc and indirectly with chelating complexes such as diaminetrimethylenepentaacetic acid using $^{111}$In, $^{90}$Y, $^{99m}$Tc, $^{186}$Re and $^{188}$Re (47,48). Antibody-mediated radiotherapy may be carried out using either beta emitting radionuclides such as $^{186}$Re, $^{188}$Re, $^{131}$I, $^{90}$Y, $^{153}$Sm, $^{32}$P or $^{109}$Pd, or with alpha particle emitters such as $^{211}$At or $^{212}$Pb, or with Auger electron emitters such as $^{125}$I or $^{123}$I (47,48). Therapy may also be attempted with either drug or toxin based conjugates for example Adriamycin-immunoconjugates (49) and vinblastine-immunoconjugates (50) have been developed. An unexpected finding of the clinical usefulness of immunoscintigraphy has been the reported complete remission of 7 out of 10 FIGO IV ovarian cancer patients who under went repeated imaging with an OC 125 antibody and had antiidiotypic HAMA (51).

Magnetic resonance imaging can be carried out using gadolinium and other lanthanides or metals such as iron conjugated to antibody based proteins. Several versions of these antibody based products are believed to be undergoing clinical evaluation and commercial development presently.

To improve the specific activity and safety of the immunoconjugate directed towards tumor markers several approaches have been taken ranging from the use of antibody fragments to genetic engineering of recombinant produced humanized antibody constructs to synthetic peptides based on the antibody epitope (52,53). Methods of antibody engineering including single chain antibodies have been well summarized by Borrebaeck (54). These improvements have improved the tumor target to background ratio and reduced the incidence of human antimouse antibody response.

The present invention provides a method for detecting, locating and treating non-prostatic endocrine tumors involving PSA as the tumor marker and optionally further optionally improves this method by first priming the endocrine tumors to produce PSA.

SUMMARY OF THE INVENTION

According to aspects of the invention, a method for detecting and locating non-prostatic endocrine cancers in vivo by injecting the human subject parenterally with an entity that has been constructed to target PSA, that is either a polyclonal or monoclonal antibody, or fragments thereof, or constructs thereof including but not limited to, single chain antibodies, bifunctional antibodies, molecular recognition units, and peptides or entities that mimic peptides, where the tumor targeting agent is labelled either directly, or indirectly with a chelating agent, with one of $^{131}$I, $^{125}$I, $^{123}$I, $^{111}$In, $^{99m}$Tc, $^{90}$Y, $^{186}$Re, $^{188}$Re, $^{32}$P, $^{153}$Sm, $^{67}$Ga, $^{201}$Tl, $^{77}$Br or $^{18}$F and is imaged with a photoscanning device, or where the tumor targeting agent is labelled with either gadolinium, terbium, tin, iron, or isotopes thereof and attached covalently to create a paramagnetic conjugate for the purpose of magnetic resonance imaging.

According to a further aspect of the invention, an in vivo method for imaging endocrine cancer in non-prostatic tissue of a patient comprises:

injecting a patient with biological binding units which bind to PSA produced by non-prostatic tissue of the patient, said PSA-binding units being labelled with imaging agents;

allowing said binding units to incubate in vivo and bind PSA associated with the endocrine cancer; and detecting presence of said imaging agents of bound units localized to said endocrine cancer.

According to another aspect of the invention, a method for detecting and locating endocrine cancers as described above, wherein the human subject is first given a steroid which induces the cancer cells to express the PSA gene.

Such method further comprises the initial step of injecting a patient with a steroid which induces the cancer cells to produce PSA, said cancer cells having receptors for the injected steroid.

According to another aspect of the invention, a method where entities constructed to target PSA as described above deliver a toxic agent which is a radioisotope that emits Auger electrons, and/or other sub-atomic particles, or toxic compounds including, but not limited to, diphtheria toxin, ricin toxin, adriamycin, chlorambucil, or daunorubicin.

According to another aspect of the invention, a method of passive immunotherapy to endocrine cancer where PSA antibodies, or constructs thereof including, but not limited to, chimeric or human antibodies, or their fragments, single chain antibodies, molecular recognition units, and peptides or entities that mimic peptides are administered parenterally.

DETAILED DESCRIPTION OF THE PREFERRED EMBODIMENTS

Figure 1A:
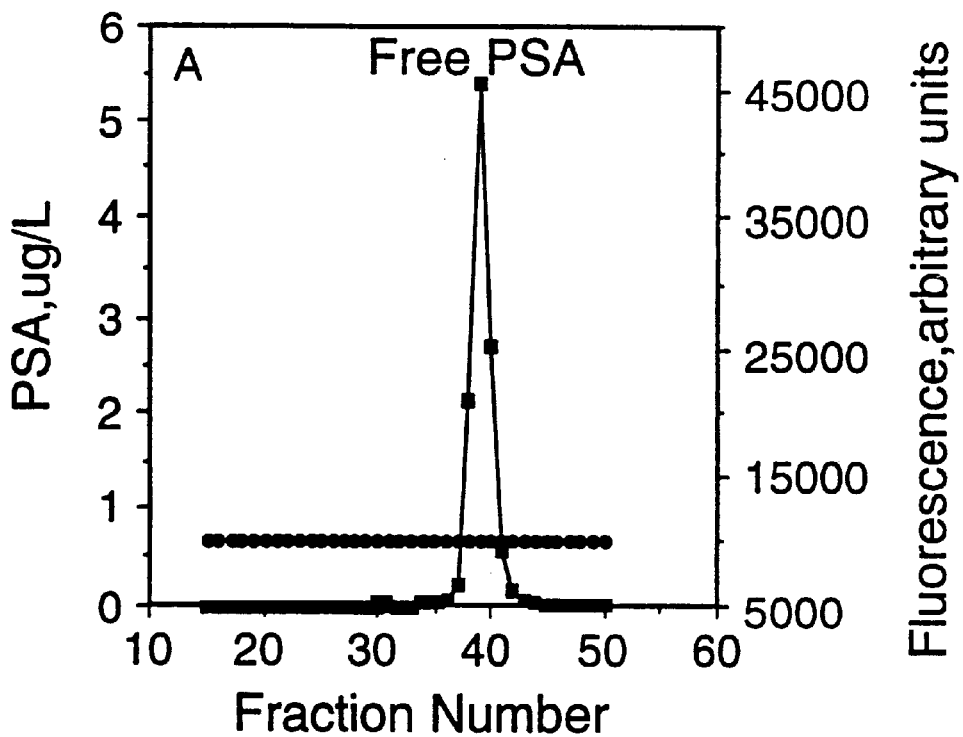
FIG. 1 is high performance liquid chromatography (HPLC) with a gel filtration column. Each HPLC fraction (0.5 mL) was analyzed with an assay that measures free and $a_1$-antichymotrypain-bound PSA (ACT-PSA) (■) or an assay that measures only ACT-PSA (♦). The response of the latter assay is in arbitrary fluorescence units since no ACT-PSA standard exists. A. Injection of purified seminal PSA which elutes at fraction 39 corresponding to a molecular weight of 33 kDa. No ACT-PSA is detected. B. Injection of a breast extract from the woman receiving the oral contraceptive Brevicon®. The PSA assay detects two peaks, one at fraction 39 (free PSA, major peak) and one at fraction 30 (100 kDa, minor peak). The latter peak is ACT-PSA as confirmed by the ACT-PSA assay. The identity of the minor peak at fraction 21 (650 kDa) is unknown. This data confirms that over 80% of the breast tissue PSA is in the free, 33 kDa form. The HPLC column was calibrated with molecular weight standards eluting at fraction 21 (660 kDa); 28 (160 kDa); 37 (44 kDa); 42 (17 kDa) and 49 (1.4 kDa).

This invention originated with the surprising discovery that the presence of PSA in human female breast is indicative of breast tumour. PSA was never thought to exist in females because PSA has always been thought to be associated with the male prostate. This discovery and its use in the prognosis of female breast cancer is described in applicant's international application PCT CA94/00267 filed May 13, 1994.

From the discovery of PSA in breast tumors, we have now determined that cancer cells with steroid receptors can be stimulated to produce PSA. It was discovered that normal breast tissue cells and non-PSA producing breast tumor cell lines (our earlier British patent application S.N. 9401491.6 filed Jan. 26, 1994) could be stimulated to produce PSA. Furthermore, non-PSA producing ovarian tumor cells could also be stimulated to produce PSA. Hence, the existence of PSA in a localized region of the body is indicative of a cancer tumor. Procedures to then image the localized concentration of PSA are therefore very useful in cancer diagnosis and prognosis.

Prior to the present invention, agents developed to target PSA were used for diagnostic and therapeutic purposes for prostate cancer only. This invention now provides for the use of radioisotopic or non-isotopic elements containing immunoconjugates directed against PSA in tumours for targeting non-prostatic endocrine cancer In vivo. The procedure is also used for the localization and monitoring of metastases by either nuclear-based gamma camera or magnetic resonance imaging. Another advantage of the invention is the application of reagents directed against PSA labelled with a therapeutically effective radionuclide, drug or toxin for the purpose of therapeutic intervention of breast cancer.

Antibodies or chemical entities created to recognize PSA are used to carry elements to image PSA secreting cancer cells and locate the disease. These antibodies or chemical entities are included in the term biological binding unit, which term is used to refer to patient compatible entities which bond to PSA and comprise antibodies or their derivatives, molecular recognition units and peptides. Antibodies encompass monoclonal and polyclonal antibodies and their derivatives and fragments and include single chain antibodies, bifunctional antibodies and other antibody constructs. Further, these biological binding units may deliver particle emitting radionuclides, drugs or toxins to promote a therapeutic effect. For example, a peptide created to recognize PSA delivering $^{188}$Re to the tumour site thereby delivers localized radiation to ablate the disease.

By way of a further example, a peptide may be developed that mimics the epitope for anti-PSA and binds to PSA and PSA receptors. This peptide may be produced on a commercially available synthesizer, using FMOC solid phase chemistry. In one application, either tyrosine, lysine, or phenylalanine is included in the peptide to which an $N_2S_2$ chelate is complexed as per U.S. Pat. No. 4,897,255. The anti-PSA peptide conjugate is then combined with a radiolabel, for example, either sodium $^{99m}$Tc pertechnetate $(Na^{99m}TcO_4)$ or sodium $^{188}$Re perrhenate$(Na^{188}ReO_4)$ and may be used to locate a PSA producing tumor.

The invention also provides the use of anti-PSA antibodies covalently combined with radioactive, cytotoxic or chemotherapeutic molecules and considers using these antibodies in immunoabsorption procedures to separate benign from malignant cells. Further, the concept of passive immunotherapy with antiidotypic antibodies is now possible.

This invention includes a method for detecting and locating non-prostatic endocrine cancers in vivo by injecting a human subject parenterally with an entity that has been constructed to target PSA, that is either a polyclonal or monoclonal antibody, or fragments thereof, or constructs thereof including, but not limited to, single chain antibodies, bifunctional antibodies, molecular recognition units, and peptides or entities that mimic peptides, where the tumour targeting agent is labelled either directly, or indirectly with a chelating agent, with one $^{131}$I, $^{125}$I, $^{123}$I, $^{111}$In, $^{99m}$Tc, $^{90}$Y, $^{188}$Re, $^{153}$Sm, $^{67}$Ga, $^{32}$P, $^{201}$Tl, $^{77}$Br or $^{18}$F and is imaged with a photoscanning device, or where the tumour targeting agent is labelled with either gadolinium, terbium, tin, iron or isotopes thereof and attached covalently to create a paramagnetic conjugate for the purpose of magnetic resonance imaging. A further application of the radioimaging technique is in the field of radioimmunoguided surgery, whereby a hand-held scintigraphic probe detector enables a surgeon to identify and remove localized metastatic disease (60).

A list of radioisotopes which can be used in the above application is as follows: $^{277}$AC, $^{211}$At , $^{128}$Ba, $^{131}$Ba, $^{7}$Be, $^{204}$Bi, $^{205}$Bi, $^{206}$Bi, $^{76}$Br, $^{77}$Br, $^{82}$Br $^{109}$Cd, $^{47}$Ca, $^{11}$C, $^{14}$C, $^{36}$Cl, $^{48}$Cr, $^{51}$Cr, $^{62}$Cu, $^{64}$Cu, $^{67}$Cu, $^{165}$Dy, $^{155}$Eu, $^{18}$F, $^{153}$Gd, $^{66}$Ga, $^{67}$Ga, $^{68}$Ga, $^{72}$Ga, $^{198}$Au, $^{3}$H, $^{166}$Ho, $^{111}$In, $^{113m}$In, $^{115m}$In, $^{123}$I, $^{125}$I, $^{131}$I, $^{189}$Ir, $^{191m}$Ir, $^{192}$Ir, $^{194}$Ir, $^{52}$Fe, $^{55}$Fe, $^{59}$Fe, $^{177}$Lu, $^{15}$O, $^{191m-191}$Os, $^{109}$Pd, $^{32}$P, $^{33}$P, $^{42}$K, $^{226}$Ra, $^{186}$Re, $^{188}$Re, $^{82m}$Rb, $^{153}$Sm, $^{46}$Sc, $^{47}$Sc, $^{72}$Se, $^{75}$Se, $^{105}$Ag, $^{22}$Na, $^{24}$Na, $^{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{166}$Yb, $^{169}$Yb, $^{175}$Yb, $^{88}$Y, $^{90}$Y, $^{62}$Zn, $^{65}$Zn.

These entities which are constructed to target PSA, as aforementioned, can also deliver a toxic agent for therapeutic purposes against breast cancer, where the toxic agent is a radioisotope that emits Auger electrons, and/or α particles, and/or β particles, and/or neutrons, and/or other sub-atomic particles, or toxic compounds including but not limited to, diphtheria toxin, ricin toxin, adriamycin, chlorambucil, or daunorubicin. Further toxins which can be used are ricin and its derivatives and fragments, Monensin, Verrucarin A, Abrin and its derivatives, Vinca alkaloids, Tricothecenes, and Pseudomonas exotoxin A. Further drugs for use as toxic agents are as follows: Leucovorin, Folinic acid, Methotrexate, Mitomycin C, Neocarzinostatin, Vinblastine, Mitomycin, Melphalan, Mechlorethamine, Fluorouracil, Fluoxuriding, Idarubicin, Doxorubicin, Epirubicin, Cisplatin, Carmustine, Cyclophosphamide, Bleomycin, Vincristine and Cytarabine.

A list of radioisotopes, which can be used for treating endocrine cancers, is as follows: $^{277}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191m}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{177m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, $^{212}$Pb.

Since PSA was found to be associated with more benign breast tumors, it was possible that PSA could be expressed by normal breasts either under physiological circumstances or after steroid hormone stimulation, such as described in the aforesaid British patent application. Cytosolic extracts were prepared as previously described (56) from eighteen normal breast tissues removed from nine women (left and right breast) during breast reduction surgery. PSA immunoreactivity was measured in these extracts using a highly specific and sensitive immunofluorometric technique (57) and by two widely used commercial PSA assays. Breast extracts from eight of the nine women were found to contain <0.03 ng of PSA per mg of total protein and were considered negative for PSA. Surprisingly, two breast extracts from the same woman (left and right breast) had relatively high concentrations of PSA (0.11 and 1.53 ng/mg). None of the eight PSA-negative women was receiving oral contraceptives or other medications. The woman with PSA-positive breasts was receiving only one medication, Brevicon®, a highly prescribed oral contraceptive containing 1 mg norethindrone (a progestin) and 0.035 mg ethinyl estradiol per tablet. The PSA-positive and negative results in the breast extracts by the immunofluorometric procedure were verified by using two widely used commercial PSA methods, namely, the IMx® from Abbott Labs, Abbott Park, Chicago, Ill. and the Tandem®-E kit from Hybritech Inc., San Diego, Calif. Additionally, one highly positive extract was serially diluted in female serum from 2- to 32-fold and analyzed by immunofluorometry and the IMx assay. Identical results were obtained.

Figure 1B:
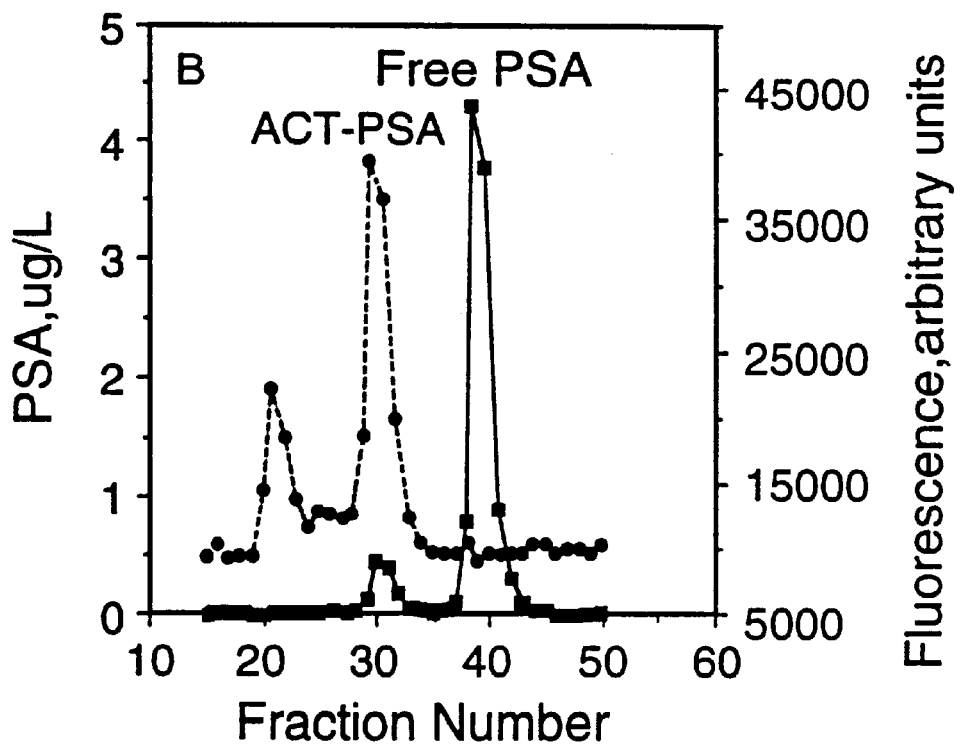
Figure 2:
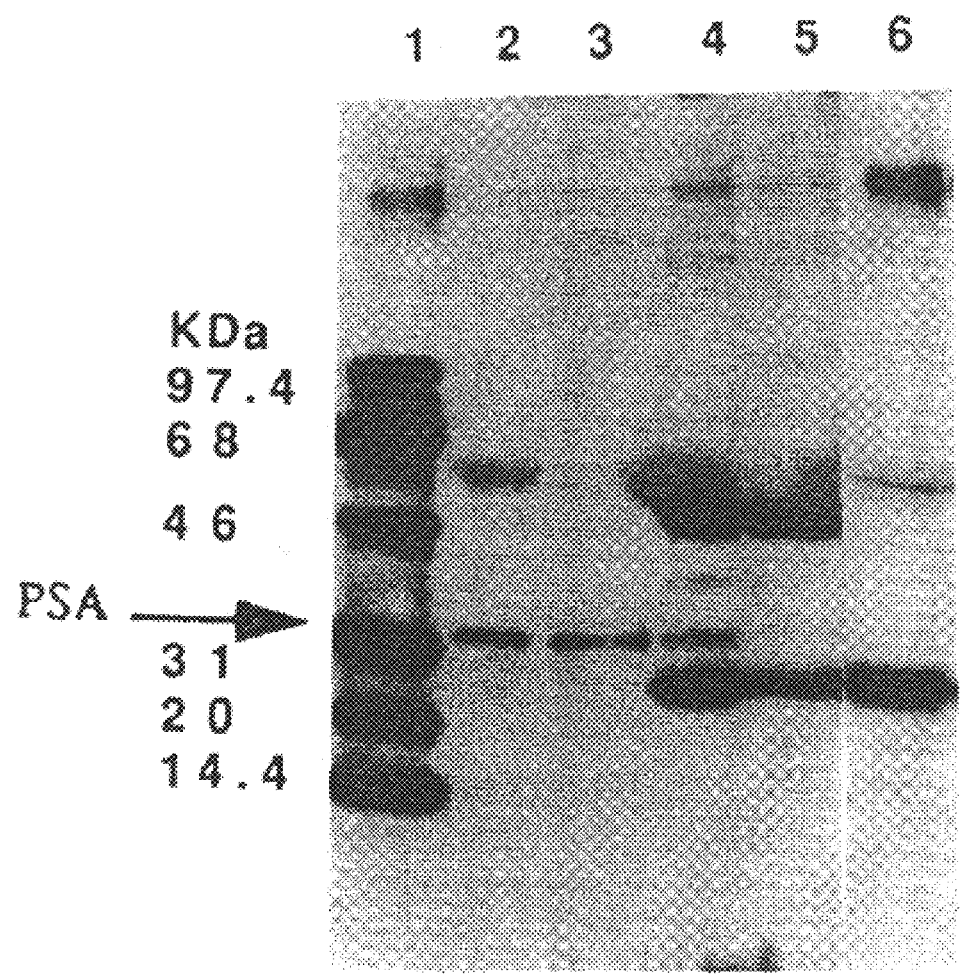
FIG. 2 is a Western blot analysis. Samples were electrophoresed on 8 to 16% gradient polyacrylamide minigels under reducing conditions, electrotransferred to nitrocellulose membranes and probed with a rabbit polyclonal anti-PSA antibody. Detection was achieved by using a horseradish peroxidase-conjugated goat anti-rabbit antibody and chemiluminescence. Lane 1. Molecular weight markers. Lane 2. Purified seminal PSA dissolved in bovine serum albumin. The PSA band appears at 33 koa (just above the 31 kDa marker). Lane 3. Supernatant from a prostatic carcinoma cell line (LNCaP) producing PSA. Lane 4. PSA-positive normal breast extract from the woman receiving Brevicon, containing a band at 33 kDa. Lane 5. Another normal breast extract tested negative for PSA by the immmunofluorometric procedure. Lane 6. An amniotic fluid tested for comparison.

The highly positive breast extract was also subjected to high performance liquid chromatography (FIG. 1) and fractions were analyzed by two immunofluorometric procedures which measure either total PSA (free PSA plus PSA bound to $a_1$-antichymotrypsin) or specifically the PSA-$a_1$-antichymotrypsin (ACT) complex (S). Over 80% of the total PSA in normal breast was in the free, 33 kDa form; a small proportion was present as PSA-ACT complex (100 kDa). Another minor species, containing PSA and ACT was also detected (660 kDa), but its identity is unknown. The presence of PSA in the highly positive breast tumor extract was further confirmed by Western blot analysis (FIG. 2). This 33 kDa form of PSA, present in normal breasts stimulated by oral contraceptives, is similar to the PSA form found in breast tumors (1). In male serum, the majority of PSA is present as PSA-ACT complex with a molecular weight of 100 kDa (57).

Figure 3:
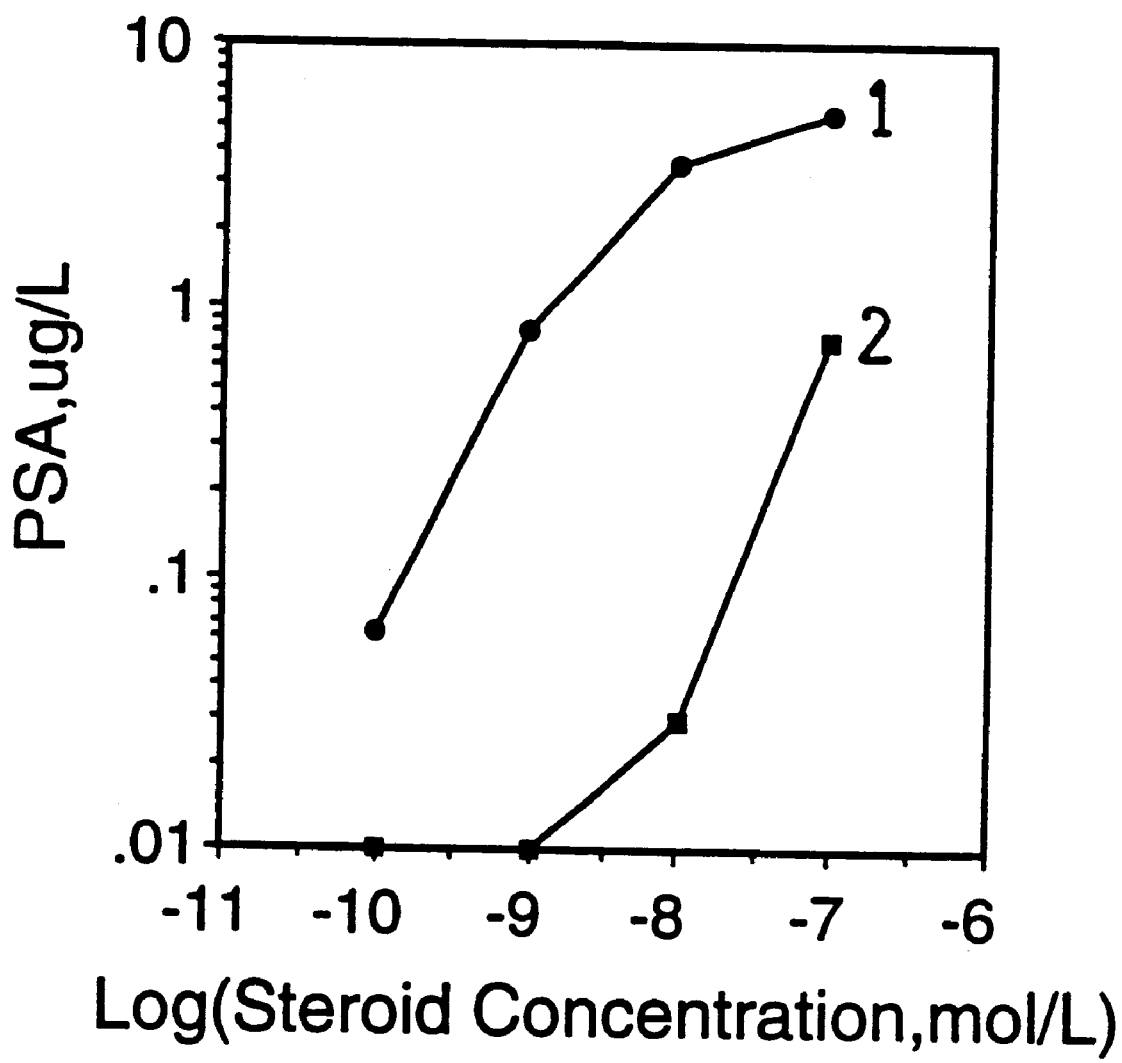
FIG. 3 is production of PSA by the breast carcinoma call line MCF-7. Cells were grown to confluency and then stimulated with varying concentrations of either norethindrone (1) or ethinyl estradiol (2) at the final concentrations indicated, in the absence of fetal calf serum from the culture medium. PSA was measured in the culture supernatant 10 days post No PSA was detected in cell cultures grown identically but either non-stimulated or stimulated with the solvent alone (ethyl alcohol). Norethindrone stimulates PSA production at concentrations as low as $10^{-10}$ M.

In order to study the oral contraceptive-induced PSA production further, T-47D and MCF-7 breast carcinoma cell lines were cultured in the absence of any steroid hormones or in the presence of norethindrone or ethinyl estradiol at various concentrations (FIG. 3). No PSA was detected in the tissue culture supernatants in the absence of steroid hormones after 11 days of confluent cultures. Ethinyl estradiol stimulated low levels of PSA production at concentrations $\geq 10^{-8}$ M. Norethindrone was effective in mediating intense PSA gene expression at concentrations as low as $10^{-10}$ M. Other progestins were also effective in mediating PSA gene expression. The identity of PSA in the. tissue culture supernatants was further characterized by HPLC and Western blot analysis as shown in FIGS. 1 and 2. Additionally, we were able to amplify by reverse transcription-polymerase chain reaction (RT-PCR), prostate specific antigen mRNA from the stimulated but not the non-stimulated cells and verify its identify by Southern hybridization and sequencing of the PCR product (58). The same procedures confirmed the presence of PSA in breast tumors positive for the protein.

We recently demonstrated that among 99 ovarian tumor extracts tested only three were positive for PSA and the concentration of the PSA was 0.048, 0.034 and 0.0076 ng/mg. Subsequently, a patient with ovarian cancer who also underwent liver transplantation and was receiving oral prednisone tablets during the period of ovarian tumor removal was tested for the presence of PSA in the ovarian tumor. Remarkably, this ovarian tumor contained 15 ng of PSA/mg protein, which is a very high amount. Combined with our previous results on breast tumor cell line tissue culture systems (British Patent Application S.N. 9401491.7) in which we found that glucocorticosteroids can stimulate PSA production, it is apparent that the ovarian tumor, generally unable to produce PSA, can be stimulated by steroids like prednisone, to produce very high levels of PSA in the tumor. The tumors, which may be imaged and treated in this invention, have steroid receptors which are stimulated in the presence of steroids to express the PSA gene and thus produce PSA. The PSA-binding units can then bind to cancer cells producing PSA which allows these cancers to be treated and localized.

Following this demonstration of stimulation of PSA gene expression in breast carcinoma cell lines and ovarian tumors, it is a further feature of the invention that stimulating cancers to express PSA would either enable detection of previously undetectable tumors or would improve radioimaging of previously detectable tumors. Indeed as shown with the normal breast tissue of the patient receiving the oral contr ceptive, steroid receptor positive tissues could be induced to produce PSA which would enable these tissues to be radioimaged. Further, the production of PSA by the non-PSA producing normal breast and ovarian tumor tissues after stimulation will enable radioimaging of non-PSA producing endocrine tumors after stimulation. While normal endocrine tissue can be stimulated to produce PSA, it will not be produced at the high levels produced by stimulated endocrine cancer cells. Thus, priming a patient with a steroid which induces PSA gene expression to, in turn, produce PSA at the tumor site, provides increased binding of the entity targeting PSA to endocrine tumors and improves the radioimaging or therapeutic delivery of toxic agents.

Figure 4:
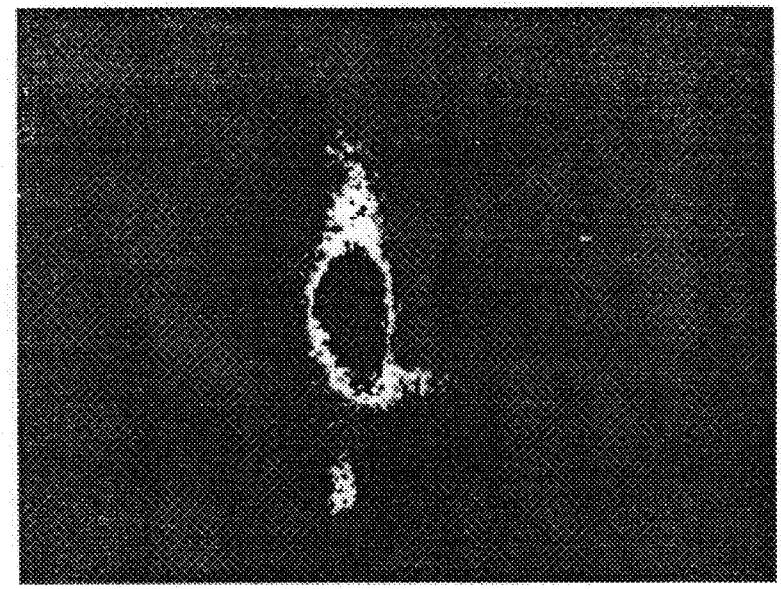
FIG. 4 is the gamma camera image of a female SCID mouse the left leg of which was injected with norgestrel-stimulated T47-D human breast cancer cells. The image was obtained 21 hours after injection of 10 MBq technetium-99m-labelled B80 anti-PSA monoclonal antibody via the tail vein. The image is an anterior view with the head at the top and the left leg extended to the side.
Figure 5:
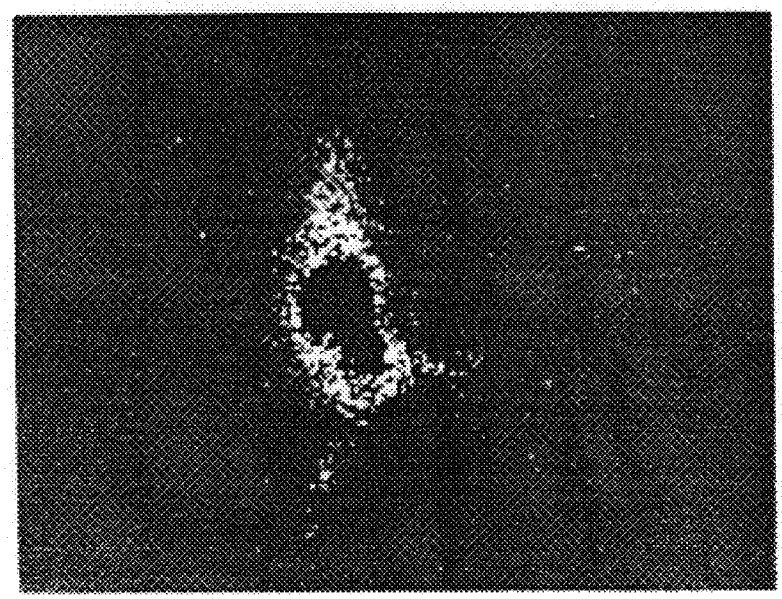
FIG. 5 is the gamma camera image of a female SCID mouse the left leg of which was injected with non-stimulated T47-D human breast cancer cells. The image was obtained 21 hours after injection of 10 MBq technetium-99m-labelled B80 anti-PSA monoclonal antibody via the tail vein. The image is an anterior view with the head at the top and the left leg extended to the side.

Gamma camera images of SCID mice with norgestrel-stimulated (FIG. 4) and non-stimulated (FIG. 5) T47-D human breast cancer cells injected into the muscle of the left leg were taken. Images were obtained 21 hours after injection of 10 MBq technetium-99m-labelled B80 anti-PSA monoclonal antibody via the tail vein. Images are anterior views, heat at top, with left leg, which contains the tumor cells, extended to the side and immobilized. An upper threshold of 5% was used to mask the residual radioactivity in the liver and the abdomen. (That is, the top 5% of counts were subtracted from all images to allow the leg tumor to be viewed.) The leg containing the tumor is seen in the lower right portion of each image. Quantification of this pair of digital images showed that the stimulated tumor contained at least 15% more radioactivity than the control tumor.

Tissue counting results were obtained for blood, normal muscle and either the stimulated or control T47-D tumor and are provided in Table 1. All values are percent injected dose per gram tissue, expressed as a mean±standard deviation for 4 animals or individual values for 2 animals. Table 1 demonstrates that the T47-D tumor cells had at least double the counts of the control. Furthermore, the stimulated tumor cells have increased counts over that of the non-stimulated tumor cells. Thus radioimaging was improved by stimulation to increase PSA production.

TABLE 1

| | |
|---|---|
| Blood | 0.96 ± 0.14 |
| Normal muscle | 0.129 ± 0.029 |
| T47-D control tumor (range 2 animals) | 0.228 – 0.231 |
| T47D- stimulated tumor (range 2 animals) | 0.266 – 0.405 |

It was proven that the norgestrel-stimulated T-47D cells in the above experiment were producing PSA from the detection of PSA in the cell culture supernatant. Furthermore, T-47D and MCF-7 tumor cell lines were injected into SCID mice to develop tumors, which mice were then injected with estrogen and/or norgestrel. The results (Table 3) demonstrated that human PSA was found in the serum of mice injected with norgestrel, however, estrogen blocked the effect of the norgestrel. Estrogen was previously shown to block the effect of progestin on PSA production in the tumor cell lines tested in our earlier British patent application S.N. 9401491.7

The breast tumor cell line tissue culture system (described in British patent application S.N. 9401491.7) suggested that any steroid having either glucocorticoid, mineralocorticoid, antiestrogen, progestin or androgen activity can regulate the PSA gene; however, estrogens cannot mediate such action. These results combined with the results from steroid stimulation of PSA expression in normal breast cells and non-PSA producing breast tumor cell lines and ovarian tumor, indicate that to stimulate tumors for radioimaging applications, any natural or synthetic steroid falling under the above categories of activity would be suitable. A list of steroids to induce expression of the PSA gene is found in Table 2.

A list of non-prostatic endocrine tumors which can be stimulated to express the PSA gene either initially or to increase PSA expression is as follows: breast tumors, ovarian tumors, lung carcinomas, meningiomas, endometrial carcinomas, colon carcinomas, salivary gland tumors, cervical carcinomas, uterine carcinomas, adrenal tumors, renal carcinomas and melanomas. The steroids, which stimulate the production of PSA, may be naturally present in the body or may be introduced artificially by injection.

An alternative aspect of this invention, as it relates to in vivo antibody binding, is a method of passive immunotherapy to non-prostatic endocrine cancer where PSA antibodies, or constructs thereof including, but not limited to, chimeric or human antibodies, or their fragments, single chain antibodies, molecular recognition units, and peptides or entities that mimic peptides are administered parenterally. Antiidiotypic antibodies may then be produced in reaction to this administration.

Antiidiotypic antibodies are antibodies directed against the idiotype (the antigen combining region or variable region) of another antibody, in this case anti-PSA antibody. These antiidiotypic antibodies in turn stimulate the production of antibodies against the idiotype of the antiidiotypic antibodies. Thus this sub-population of antiidiotypic antibodies bind the initial antigen, PSA. For example, human anti-PSA antibodies can be administered to patients that have PSA secreting breast tumors. A dose escalating regime can be followed, over a period of months, if there is an absence of any untoward response. Patient sera can be examined via in vitro methods for the development of antiidiotypic antibodies. The development of anti-idiotypic antibodies results in enhancement or beneficial modification of the patient's immune response and thereby elicits an anti-tumor response (51).

EXAMPLE 1

Breast tumors were snap-frozen in liquid nitrogen. Frozen sections (5 μm thick) were placed on clean glass slides and processed for immunohistochemistry. Slides to be stained for PSA were fixed immediately in 10% buffered formalin for 10 min. and then placed in phosphate-buffered saline. Staining was performed with a polyclonal anti-PSA antibody from Medix Biotech, Foster City, Calif. and further completed by use of the avidin-biotin technique (ABC) using a kit from Vector Laboratories, Burlingame, Calif. Immunoperoxidase staining was, according to the manufacturer's recommendation (58). Tumors positive or negative for PSA by the immunofluorometric procedure were used. The slides were examined under a light microscope. Tumors, negative for PSA showed no staining while tumors positive for PSA exhibited strong brown cytoplasmic staining with the immunoperoxidase technique. This experiment demonstrated that PSA in breast tumors can be localized by antibodies against PSA.

EXAMPLE 2

Cell Preparation

The following cell line was obtained from the ATCC: T47-D, an estrogen dependent cell line derived from breast cancer. The cell line was checked for freedom from microbial contaminants and all operations were carried out aseptically. T47-D cells were cultured in α Medium with 10% fetal calf serum in sterile culture flasks. Cells were then incubated at 37° C. and growth was checked visually using a microscope. Two sets of T47-D cells were prepared, one set stimulated with norgestrel, a progestin, and the other set non-stimulated. The stimulated set were stimulated with a solution of norgestrel (concentration 1 millimole in ethanol), at the concentration of 1 micromolar in fresh media for a period of 48 h. PSA was detected in the supernatant of the norgestrel-stimulated cells' supernatant after 72 h and the concentration of PSA increased from 0.013 μg/L to 0.036 μg/L at 96 h.

Cells were scraped into a centrifuge tube and spun down in a laboratory centrifuge at approximately 240 G for six minutes. Cells were re-suspended using the sterile culture medium and re-spun, the procedure was repeated a total of three times. For a 0.2 ml pellet of cells, 0.1 ml was injected subcutaneously into the left leg, slightly below the knee, in female SCID mice. The amount of cells injected into the SCID mice were estimated to be between $2.5 \times 10^6$ and $1 \times 10^7$. The experiment was repeated once using trypsin to avoid clumping of the harvested cells, in which case the stimulation with norgestrel was increased to 2 micromolar in fresh culture medium to overcome any effect due to trypsin. The results of imaging shown in FIG. 4 and 5 were obtained using cells harvested by scraping, whereas the results of Table 1 were obtained using cells harvested with trypsin.

Preparation of the Monoclonal Antibody

The anti-PSA monoclonal antibody, B 80, was obtained from Biomira Inc., Edmonton, Alberta. The antibody was prepared for radioimaging using the method described by Joiris et al. (55) with 2 iminothiolane. Three solutions are first prepared: 5 milligram/ml solution of B 80 in physiological saline; 10 milligram/ml solution of 2 iminothiolane; and a phosphate buffer solution containing 0.25M of phosphate adjusted to pH 7.4. 10 microliters of each of these solutions was combined and allowed to stand for 30 minutes at about 25° C. This solution was then combined with 100 microliters of $^{99m}TcO_4^-$ (approximately 10 mCi/ml or 370.4 MBq/mL) and 100 microliters of a dilute stannous glucoheptonate solution containing 5 micrograms of stannous chloride. This solution was allowed to incubate for 10 minutes at 25° C. The solution was then purified using a Sephadex G-50 column which has been pre-blocked with a 1% solution of human serum albumen in 0.9% NaCl. The column was eluted using 0.9% NaCl. The hottest fraction, as determined by measurements using a Capintec Dose Calibrator was kept and diluted to 50 Mbq/ml using 0.9% NaCl. 0.2 ml, a solution equal to 10 MBq was the injected dose.

Imaging Studies 0.2 ml of $^{99m}Tc$ radiolabelled B 80 antibody was injected intravenously into the tail vein of the SCID mice prepared as described above. Imaging studies were carried out using a Siemans Orbiter, model 7400 gamma camera with a low energy all purpose collimator using a magnification factor of 2.5. Data was collected using a Picker PCS I–II nuclear medicine computer. Counts were obtained using a 128×128 matrix. Imaging studies were carried out with the mouse conscious in a lucite restraining device with the leg containing the tumor taped to the base plate. The restraining device was placed directly on the collimator. Initial images were carried out between 1 and 7 hours post injection using a five minute data acquisition and repeated at 20 hours using a 15 minute acquisition. Quantification was performed by drawing a region of interest around the tumor. After correction for background counts, comparisons of the norgestrel-stimulated and control tumors were made using counts per pixel values.

Following the final imaging session, the mice were sacrificed by cervical dislocation and samples of blood, leg muscle containing tumor cells, and control muscle from the opposite leg were obtained, weighed and assayed in a gamma well counter (Capintec). From the knowledge of the dose administered and counting efficiency, the percent dose per gram was calculated.

EXAMPLE 3

T-47D tumor cells or MCF-7 tumor cells were implanted into SCID mice and left to develop as tumors over several weeks. Mice were injected subcutaneously with estrogen and/or norgestrel in ethanol (100 μL of a $10^{-3}$ M solution per mouse) and serum was collected after 48 hours. The results from measuring PSA within the serum by the fluorescence method (57) are found in Table 3.

TABLE 3

| Experiment | Tumor Type | Estrogen | Norgestrel | Serum PSA Assay, Fluorescence |
|---|---|---|---|---|
| 1 | T-47D | − | + | 2818 |
| 2 | T-47D | + | + | 2661 |
| 3 | MCF-7 | + | + | 1912 |
| 4 | MCF-7 | − | + | 6893 |
| 5 | MCF-7 | + | − | 2067 |
| 6 | MCF-7 | − | + | 2642 |

TABLE 2

LIST OF STEROIDS

3β-Acetoxy-9(11),16-allopregnidien-20-one
21-Acetoxyallopregnan-3,20-dione
3β-Acetoxy-5-androsten-17-one
3β-Acetoxybisnor-5-cholenic acid
21-Acetoxy-3α-17-dihydroxy-5β-pregnan-11,20-dione
3α-Acetoxy-5β-etianic acid
3β-Acetoxy-5β-etianic acid
3β-Acetoxy-5-etienic acid
3β-Acetoxyetiocholenic acid
21-Acetoxy-17-hydroxyallopregnan-3,11,20-trione
3β-Acetoxy-5,16-pregnadien-20-one
12α-Acetoxypregnan-3,20-dione
21-Acetoxypregnanedione
Acetoxypregnanolone
17-Acetoxypregnenolone
21-Acetoxypregnenolone
3β-Acetoxy-16,(5β)-pregnen-20-one
11α-Acetoxyprogesterone
17-Acetoxyprogesterone
17-Acetoxyprogesterone 3-ethyleneketal
21-Acetoxyprogesterone
Δ1-Adrenosterone
Adrenosterone
Aetiocholane
Aldosterone
Aldosterone 21-acetate
Aldosterone 3-CMO
Aldosterone 3-CMO: BSA
Aldosterone 18,21-diacetate
Aldosterone diacetate 3-CMO
Aldosterone diacetate 3-CMO: BSA
Aldosterone 21-hemisuccinate
Aldosterone 21-hemisuccinate: BSA
Allocholesterol
Allodihydrocorticosterone
Allodihydrocortisol
Allodihydrocortisone
Allodihydrocortisone acetate
Allodihydro substance "S"
Allodihydrotestosterone
Allopregnanediol
Allopregnanolone
Allopregnanolone acetate
Allotetrahydro compound "A"
Allotetrahydro compound "B"
Allotetrahydro compound "E"
Allotetrahydro compound "F"
Allotetrahydrocorticosterone
Allotetrahydrocortisol
Allotetrahydrocortisone
Allotetrahydro-11-dehydrocorticosterone
Allotetrahydrodesoxycorticosterone
Allotetrahydrodesoxycorticosterone 21-acetate
Allotetrahydro-11-desoxycortisol
Allotetrahydro DOC
Allotetrahydro DOC 21-acetate
Allotetrahydrohydrocortisone
Allotetrahydro substance "Q".
Allotetrahydro substance "S"
Allo TH "A"
Allo TH "B"
Allo TH "E"
Allo TH "E" diacetate
Allo TH "F"
Allo TH "F" diacetate
Allo TH "S"

TABLE 2-continued

LIST OF STEROIDS

Androstadienedione
Androstadienedione 3-erhylenoI erher
Androstanedione
Androstanolone
Androstatriendione
Androstenediol
Androstenedione
Androstenolone
4-Androsten-17β-ol-one enol diacetate
Androsterone
Androsterone acetate
Androsterone benzoate
Androsterone chloroformate
Androsterone-CMO
Androsterone glucuronide
Androsterone hemisuccinate
Androsterone propionate
Androsterone sodium sulfate
Androsterone tosylate
Anhydroxyprogesterone
Apocholic acid
Beclomethasone
Beclomethasone 21-acetate
Beclomethasone 17,21-dipropionate
Beclomethasone 21-hemisuccinate
Beclomethasone 21-propionate
Betamethasone
Betamethasone 21-acetate
Betamethasone 17,21-dipropionate
Betamethasone 21-disodium phosphate
Betamethasone 21-hemisuccinate
Betamethasone 17-valerate
3,4-Bis(4-hydroxyphenl)-hexane
3,4-Bis-(4-hydroxyphenyl)-3-hexene
Bolderone
Bolderone sulfate, sodium salt
2α-Bromo-5α-cholestan-3-one
4-Bromoequilenin
4-Bromoequilin
2-Bromoestradiol
4-Bromoestradiol
16α-Bromoestradiol
16α-Bromo-17α-estradiol
16α-Bromoestrone
16β-Bromoestrone
2-Bromoethynylestradiol
4-Bromoethynylestradiol
17-Bromopregnenolone
17-Caproxyprogesterone
Chenodeoxycholic acid
Chenodeoxycholic acid 3-Hemisuccinate
Chenodeoxycholic acid methyl ester
Chenodeoxycholic acid sodium salt
3β-Chloro-5α-cholestane
3β-Chloro-5-cholestene
21-Chloro-17-hydroxyprogesterone
Cholaic acid
α-Cholestanol
β-Cholestanol
Cholestanol
Cholestanol acetate
Cholestanol benzoate
Cholestanol hemisuccinate
Cbolestanol propionate
Cholestanol rosylate
5-Cholestan-3β-ol chloride
Cholestanone
5α-Cholestan-3-one enol acetate
5α-Cholestan-3β-yl chloride
Cholestanyl chloride
Cholestene
Cholestenol
5-Cholesten-3β-yl chloride
Cholestenone
4-Cholesten-3-one enol acetate
Cholesterilene
Cholesterin

TABLE 2-continued

LIST OF STEROIDS

Cholesterol
Cholesteryl acetate
Cholesteryl acetoacetate
Cholesteryl benzoate
Cholesteryl n-butyrate
Cholesteryl caprylate
Cholesteryl chloride
Cholesteryl chloroacetate
Cholesteryl chloroformate
Cholesteryl cinnamate
Cholesteryl n-decylate
Cholesteryl ethylether
Cholesteryl formate
Cholesteryl glucuronide, sodium salt
Cholesteryl hemisuccinate
Cholesteryl heptanoate
Cholesteryl hexadecanoate
Cholesteryl hydrocinnamate
Cholesteryl hydrogen phthalate
Cholesteryl iso-butytate
Cholesteryl laurate
Cholesteryl methylcarbonate
Cholesteryl methyl echer
Cholesteryl myristate
Cholesteryl nonanoate
Cholesteryl octanoate
Cholesteryl pelargonate
Cholesteryl β-phenylpropionate
Cholesteryl n-propionate
Cholesteryl pyridinium sulfate
Cholesteryl sodium sulfate
Cholesteryl stearate
Cholesteryl rosylate
Cholesteryl valerate
Cholic acid
Cholic acid methyl ester
Cholic acid sodium salt
Cinchol
Cistestosterone
Coprostane
Coprostanol
Coprostanol acetate
Coprostanol benzoate
Coprostan-3-one
Coprostenol
Coprosterol
Cortexolone
Cortexone
Corticosterone
Corticosterone acetate
Corticosterone 21-acetate, 3-CMO
Corticosterone 21-acetate, 3-CMO: BSA
Corticosterone 3-CMO
Corticosterone 3-CMO: BSA
Corticosterone diethyleneketal
Corticosterone hemisuccinate
Corticosterone hemiuccinate: BSA
Cortisol
Cortisol acetate
Cortisol 21-acetate, 3-CMO
Cortisol 21-acetate, 3-CMO: BSA
Cortisol 3-CMO
Cortisol 3-CMO: BSA
Cortisol glucuronide
Cortisol glucuronide, sodium salt
Cortisol hemisuccinate
Cortisol 17-valerate
Δ1-Cortisone
Cortisone
Cortisone acetate
Cortisone 21-acetate, 3-CMO
Cortisone 21-acetate, 3-ethyleneketal
Cortisone diethyleneketal
Cortisone 21-hemisuccinate
Cortisone 21-sodium sulfate
Cortol
β-Cortol

TABLE 2-continued

LIST OF STEROIDS

Cortolone
β-Cortolone
DES
DHEA
DHEA acetate
DOCA
DOCA 3-ethyleneketal
DOC 21-aldehyde hemiacetal
DOC 3-CMO
DOC 3-CMO: BSA
DOC glucuronide
DOC hemisuccinate
DOC propionate
DPA
16-Dehydroallopregnanolone
16-Dehydroallopregnanolone acetate
24-Dehydrocholesterol
Dehydrocholic acid
1-Dehydrocortisone
11-Dehydrocorticosterone
11-Dehydrocorticosterone acetate
11-Dehydrocorticosterone hemisuccinate
Dehydrocortisol
Dehydroepiandrosterone
Dehydroepiandrosterone acetate
Dehydroepiandrosterone glucuronide
Dehydroepiandrosterone potassium sulfate
Dehydroepiandrosterone propionate
Dehydroepiandrosterone sodium sulfate
Dehydroepiandrosterone tosylate
6-Dehydro-17α-etradiol
6-Dehydroestradiol
6-Dehydroestradiol diacetate
7-Dehydro-17α-estradiol
7-Dehydro-17β-estradiol
7-Dehydro-17β-estradiol diacetate
16-Dehydroestradiol diacetate
6-Dehydroestrone
6-Dehydroestrone acetate
6-Dehydroestrone benzoate
6-Dehydroestrone benzyl ether
6-Dehydroestrone methyl ether
8-Dehydroestrone
Dehydroisoandrosterone
Dehydroisoandrosterone acetate
1-Dehydromethyltestosterone
16-Dehydro-5α-pregnan-3β-ol 11,20-dione
16-Dehydro-5α-pregnan-3β-ol 11,20-dione acetate
16-Dehydropregnanolone
16-Dehydropregnanolone acetate
16-Dehydro-5α-pregnan-3β-ol 20-one
16-Dehydro-5α-pregnan-3β-ol 20-one acetate
16-Dehydro-5β-pregnan-3β-ol 20-one
16-Dehydro-5β-pregnan-3β-ol 20-one acetate
16-Dehydropregnenolone
16-Dehydropregnenolone acetate
16-Dehydropregnenolone acetate, oxime
16-Dehydropregnenolone oxime
16-Dehydroprogesterone
16-Dehydrorestosterone
1-Dehydrotestosterone acetate
1-Dehydrotestosterone benzoate
1-Dehydrotestosterone 3-CMO
1-Dehydrotestosterone hemisuccinate
1-Dehydrotestosterone propionate
1-Dehydrotestosterone sodium sulfate
6-Dehydrotestosterone
6-Dehydrotestosterone acetate
6-Dehydrotestosterone benzoate
6-Dehydrotestosterone 3-CMO
6-Dehydrotestosterone hemisuccinate
6-Dehydrotestosterone propionate
Deoxycholic acid
Deoxycholic acid diacetate
Deoxycholic acid sodium salt
Desmosterol
Desmosterol acetate Desonide
Desoxycorticosterone
Desoxycorticosterone acetate
Desoxycorticosterone acetate 3-CMO
Desoxycorticosterone acetate 3-CMO: BSA
Desoxycorticosterone acetate, 3-ethyleneketal
Desoxycorticosterone 21-aldehyde hemiacetal
Desoxycorticosterone 3-CMO
Desoxycorticosterone 3-CMO: BSA
Desoxycorticosterone glucuronide
Desoxycorticosterone hemisuccinate
Desoxycorticosterone propionate
11-Desoxycortisol
21-Desoxycortisol
21-Desoxycortisone
17-Desoxycortol
17-Desoxy-β-cortol
17-Desoxyβ-cortolone
11-Desoxy-17-hydroxycorticosterone
Desoxymethasone
Dexamethasone
Dexamethasone acetate
Dexamethasone hemisuccinate
Dexamethasone hemisuccinate: BSA
Dexamethasone 21-mesylate
Dexamethasone phosphate disodium salt
Dianabol
2,4-Dibromoestradiol
Dichlorisone
3α, 12α-Diformyloxydesoxycholic acid
Dihydroandrosterone
Dihydrocholesterol
Dihydrocholesterol acetate
Dihydrocholesterol benzoate
Dihydrocholesterol hemisuccinate
Dihydrocholesterol methyl ether
Dihydrocholesterol propionate
Dihydrocholesterol tosylate
5α-Dihydrocortexone
5α-Dihydrocorticosterone
5α-Dihydrocortisol
5α-Dihydrocortisone acerate
20β-Dihydrocorticosterone
20β-Dihydrocortisol
Dihydrocortisone
5α-Dihydrocortisone
5β-Dihydrocortisone
Dihydrocortisone acetate
5α-Dihydro-11-dehydrocorticosterone
Dihydro-11-desoxycortisol
17β-Dihydroequilenin
17β-Dihydroequilenin diacetate
17α-Dihydroequilin
17β-Dihydroequilin
17β-Dihydroequilin diacetate
20β-Dihydro Kendall's compound "B"
5α-Dihydro substance "Q"
5α-Dihydro substance "S"
5α-Dihydrotestosterone
Dihydrotestosterone
Dihydrotestosterone acetate
Dihydrotestosterone benzoate
Dihydrotestosterone 3-CMO
Dihydrotestosterone 3-CMO: BSA
Dihydrotestosterone chloroformate
Dihydrotestosterone cyclopentylpropionate
Dihydrotestosterone enanthate
Dihydrotestosterone glucuronide
Dihydrotestosterone hemisuccinate
Dihydrorestosterone hemisuccinate: BSA
Dihydrotesrosterone hexahydrobenzoate
Dihydrotestosterone propionate
Dihydrotestosterone tosylate
5β-Dihydrorestosterone
5β-Dihydrotesrosterone acetate
5β-Dihydrotesrosterone 3-CMO
5β-Dihydrotestosterone hemisuccinate

TABLE 2-continued

LIST OF STEROIDS

5β-Dihydrotesrosterone propionate
3α,12α-Dihydroxycholanic acid
5β-Dihydroxycorticosterone
3α,7α-Dihydroxy-12-ketocholanic acid
3α,12α-Dihydroxynorcholanate
3β,17-Dihydroxy-5-pregnen-3-one
Dihydro Reichstein's substance "S"
3,6-Diketocholanic acid
3,7-Diketocholanic acid
3,12-Diketocholanic acid
7,12-Diketolithocholic acid
7,12-Diketolithocholic acid sodium salt
6,16-Dimethyl-16-dehydroprogesterone
2,4-Dinitroestradiol
Diosgenin
Diosgenin acecate
Diosgenin benzoate
E 1
E 2
E 3
E 4
α-Ecdysone
Electrocortin
Epi-allocholesterol
Epi-allotetrahydro "B"
Epiandrosterone
Epiandrosterone acetate
Epiandrosterone benzoate
Epiandrosterone chloroformate
Epiandrosterone 17-CMO
Epiandrosterone glucuronide
Epiandrosterone hemisuccinate
Epiandrosterone potassium sulfate
Epiandrosterone propionate
Epiandrosterone sodium sulfate
Epiandrosterone tosylate
Epicholestanol
Epicholesterol
Epi compound "F"
Epicoprostanol
Epicoprostanol acetate
Epicoprostanol benzoate
Epicoprostanol hemisuccinate
Epicoprostanol propionate
Epicoprosterol
Epidihydrocholesterol
16-Epiestriol
16-Epiestriol 3-methylether
16-Epiestriol triacetate
17-Epiestriol
17-Epiestriol triacetate
16,17-Epiestriol
16,17-Epiestriol triacetate
Epitestosterone
Epitestosterone acetate
Epitestosterone benzoate
Epitestosterone hemisuccinate
11-Epi Tetrahydro compound "B"
11-Epi-Tetrahydro compound "F"
11-Epi-Tetrahydrocorticosterone
11-Epi-Tetrahydrocortisol
11-Epi-Tetrahydrohydrocortisone
11-Epi-TH "B"
11-Epi-TH "F"
Epoxypregnanolone
Epoxypregnenolone
Epoxypregnenolone acetate
16α,17-epoxyprogesterone
d-Equilenin
d-Equilenin acetate
d-Equilenin benzoate
d-Equilenin benzyl ether
d-Equilenin etheyl ether
d-Equilenin methyl ether
Equilin
Equilin acetate
Equilin benzoate
Equilin methylether
4,22-Ergostadien-3-one
Ergosterol
Esmilagenin
Estetrol
17α-Estradiol
17α-Estradiol 3-acetate
17α-Estradiol 17-acetate
17α-Estradiol diacecate
17β-Estradiol
17β-Estradiol 3-acetate
17β-Estradiol 17-acetate
17β-Estradiol 17-acetate, 3-benzoate
17β-Estradiol 17-acetate, 3-methyl ether
17β-Estradiol 3-benzoate
17β-Estradiol 3-benzoate, 17-valerate
17β-Estradiol 3-benzyl ether
17β-Estradiol 17-cyclopentylpropionate
17β-Estradiol diacetate
17β-Estradiol dibenzoate
17β-Estradiol dicyclopentylpropionate
17β-Estradiol diglucuronide
17β-Estradiol dihemisuccinate
17β-Estradiol dipalmitate
17β-Estradiol diphosphate, disodium salt
17β-Estradiol dipropionate
17β-Estradiol disodium sulfate
17β-Estradiol 17-enanthate
17β-Estradiol 3-glucuronide
17β-Estradiol 17-glucuronide
17β-Estradiol 3-hemisuccinate
17β-Estradiol 17-hemisuccinate
17β-Estradiol 17-hemisuccinate: BSA
17β-Estradiol 17-hexahydrobenzoate
17β-Estradiol 3-methyl ether
17β-Estradiol 17-phenylpropionate
17β-Estradiol 3-phosphate, disodium salt
17β-Estradiol 17-phosphate, disodium salt
17β-Estradiol 3-sodium sulfate
17β-Estradiol 17-sodium sulfate
17β-Estradiol 17-stearate
17β-Estradiol 17-valerate
Estriol
Estriol 3-acetate
Estriol 16-acetate
Estriol 16,17-diacetate
Estriol 3,17-disodium sulfate
Estriol 16,17-disodium sulfate
Estriol 3-glucuronide, sodium salt
Estriol 3-hemisuccinate
Estriol 16-hemisuccinate
Estriol 3-methyl ether
EsEriol 3-phosphate, disodium salE
Estriol 3-sodium sulfate
Estriol 17-sodium sulfate
Estriol triacetate
Estriol tripropionate
Estrone
Estrone acetate
Estrone benzoate
Estrone benzyl ether
Estrone 17-enol acetate, 3-methyl ether
Estrone enol diacetate
Estrone ethyl ether
Estrone glucuronide, sodium salt
Estrone hemisuccinate
Estrone methoxime
Estrone methyl ether
Estrone phosphate, disodium salt
Estrone propionate
Estrone trimethylacetate
Ethisterone
24b-Ethylcholesterol
17α-Ethyl-19-nor-testosterone
Ethynodiol
Ethynylandrostanolone
Ethynylandrostendiol

TABLE 2-continued
LIST OF STEROIDS

Ethynylandrostenolone
17α-Ethynyldihydrotestosterone
Ethynylestradiol
17α-Ethynylestradiol 3-acetate
Ethynylestradiol 3-methyl ether
17α-Ethynyl-19-nor-testosterone
Ethynyltestosterone
Etiadienic acid
Etiadienic acid 3-acetate
Etiadienic acid methyl ester
Etianic acid
Etienic acid
Etienic acid acetate
Etienic acid methyl ester
Etiocholane
Etiocholan-3α,17α-diol
Etiocholan-3α,17β-diol
Etiocholan-3α,17β-diol diacetate
Etiocholan-3β,17α-diol
Etiocholan-3β,17β-diol
Etiocholan-3β,17β-diol diacetate
Etiocholan-3α,6α-diol-17-one
Etiocholan-3α,11β-diol-17-one
Etiocholan-3,17-dione
Etiocholan-3α-ol
Etiocholan-3α-ol-11,17-dione
Etiocholanolone
Etiocholanolone acetate
Etiocholanolone benzoate
Etiocholanolone 17-CMO
Etiocholanolone glucuronide
Etiocholanolone hemisuccinate
Etiocholanolone potassium sulfate
Etiocholanolone propionate
Etiocholanolone sodium sulfate
Etiocholan-3β-ol-17-one
Etiocholan-17β-ol-13-one
Etiocholan-3β-ol-17-one acetate
Etiocholan-3β-ol-17-one benzoate
Etiocholan-3β-ol-17-one hemisuccinate
Etiocholan-3β-ol-17-one propionate
Etiocholenic acid acetate
Flucinonide
Flumethasone
Fluocinolone acetonide
2-Fluoroestradiol
Fluorometholone
Fluoxymesterone
Flurandrenolide
Flurocortisone
Fucosterol
Glycochenodeoxycholic acid
Glycochenodeoxycholic acid sodium salt
Glycocholanic acid
Glycocholic acid
Glycocholic acid potassium salt
Glycocholic acid sodium salt
Glycodehydrocholic acid
Glycodehydrocholic acid sodium salt
Glycodeoxycholic acid
Glycodeoxycholic acid sodium salt
Glycohyodeoxycholic acid
Glycohyodeoxycholic acid sodium salt
Glycolithocholic acid
Glycolithocholic acid sodium salt
Hecogenin
Hecogenin acetate
Hetero-1-methylestradiol diacetate
6β-Hydrocortisol
Hydrocortisone
11α-Hydrocortisone
Hydrocortisone acetate
Hydrocortisone acetate, 3-CMO
Hydrocortisone acetate, 3-CMO: BSA
Hydrocortisone 3-CMO
Hydrocortisone 3-CMO: BSA
Hydrocortisone glucuronide
Hydrocortisone hemisuccinate
Hydrocortisone hemisuccinate: BSA
3β-Hydroxy-5α-androstan-17-one
4-Hydroxyandrostenedione
7α-Hydroxyandrostenedione
19-Hydroxy-4-androsten-3,17-dione
17β-Hydroxy-4-androsten-3-one
16α-Hydroxyandrosterone
3β-Hydroxy nor-5-cholenic acid
3β-Hydroxy- cholenic acid
4β-Hydroxycholesterol
7α-Hydroxycholesterol
7β-Hydroxycholesterol
19-Hydroxycholesterol
20α-Hydroxycholesterol
25-Hydroxycholesterol
Hydroxycholic acid
6β-Hydroxycorticosterone
17-Hydroxycorticosterone
6β-Hydroxycortisol
18-Hydroxy-11-deoxycorticosterone
3α-Hydroxy-7,12-diketocholanic acid
18-Hydroxy DOC
2-Hydroxyestradiol
2-Hydroxyestradiol 17-acetate
2-Hydroxyestradiol 3-methyl ether
4-Hydroxyestradiol
6α-Hydroxyestradiol
11α-Hydroxyestradiol
16α-Hydroxy-17β-estradiol
16β-Hydroxy-17β-estradiol
2-Hydroxyestriol
15α-Hydroxyestriol
2-Hydroxyestrone
4-Hydroxyestrone
16α-Hydroxyestrone
2-Hydroxyestrone-3-methyl ether
3β-Hydroxy-5α-etianic acid
3β-Hydroxy-5α-etianic acid methyl ester
3α-Hydroxy-5β-etianic acid
3α-Hydroxy-5β-etianic acid methyl ester
3β-Hydroxy-5β-etianic acid
3β-Hydroxy-5β-etianic acid methyl ester
11β-Hydroxyetiocholanolone
16α-Hydroxyetiocholanolone
3β-Hydroxy-5-etiocholenic acid
3α-Hydroxy-6-ketocholanic acid
11α-Hydroxymethyltestosterone
6β-Hydroxyprednisolone
17-Hydroxypregnanolane
16α-Hydroxypregnenolone
17-Hydroxypregnenolone
17-Hydroxypregnenolone 3-acetate
21-Hydroxypregnenolone
2α-Hydroxyprogesterone
6α-Hydroxyprogesterone
6β-Hydroxyprogesterone
6β-Hydroxyprogesterone acetate
6β-Hydroxyprogesterone hemisuccinate
6β-Hydroxyprogesterone hemisuccinate: BSA
11α-Hydroxyprogesterone
11α-Hydroxyprogesterone acecate
11α-Hydroxyprogesterone hemisuccinate
11α-Hydroxyprogesterone hemisuccinate: BSA
11α-Hydroxyprogestrone tosylate
11β-Hydroxyprogestrone
12α-Hydroxyprogestrone
17-Hydroxyprogestrone
17-Hydroxyprogestrone 3-CMO
17-Hydroxyprogestrone 3-CMO: BSA
18-Hydroxyprogestrone
19-Hydroxyprogestrone
20α-Hydroxyprogestrone
20β-Hydroxyprogestrone
21-Hydroxyprogestrone
6β-Hydroxytestosterone
7α-Hydroxytestosterone

TABLE 2-continued

LIST OF STEROIDS

11α-Hydroxytestosterone
11α-Hydroxytestosterone hemisuccinate
11α-Hydroxytestosterone hemisuccinate: BSA
11β-Hydroxytestosterone
16α-Hydroxytestosterone
16β-Hydroxytestosterone
19-Hydroxytestosterone
11α-Hydroxytigogenin
Hyocholic acid
Hyocholic acid methyl ester
Hyodeoxycholic acid
Hyodeoxycholic acid methyl ester
Iodocholestrol
Isoallospirostan-3β,12β-diol
Isoandrosterone
14-iso-Equilenin acetate
14-iso-Equilenin methyl ether
Isoergosterone
Iso-Sarsasapogenin
Kendall's compound "A"
Kendall's compound "B"
Kendall's compound "C"
Kendall's compound "E"
Kendall's compound "E" acetate
Kendall's compound "F"
Kendall's compound "G"
Kendall's compound "H"
Kendall's desoxy compound "B"
11-Ketoandrosterone
Ketocholanic acid
3-Ketocholanic acid
6-Ketocholestanol
6-Ketocholestanol acetate
7-Ketocholestanol
6-Ketocholestenone
7-Ketocholesterol
7-Ketocholesterol acetate
18-Ketocorticosterone
7-Ketodeoxycholic acid
6-Keto-17α-estradiol
6-Keto-17α-estradiol 6-CMO
6-Keto-17α-estradiol 6-CMO: BSA
6-Keto-17β-estradiol
6-Keto-17β-estradiol 6-CMO
6-Keto-17β-estradiol 6-CMO: BSA
16-Keto-17β-estradiol
6-Ketoestriol 6-CMO
6-Ketoestriol 6-CMO: BSA
6-Ketoestriol triacetate
6-Ketoestrone
6-Ketoestrone acetate
6-Ketoestrone 6-CMO
6-Ketoestrone 6-CMO: BSA
16-Ketoestrone
6-Ketoethynylestradiol
6-Ketoethynylestradiol 6-CMO
6-Ketoethynylestradiol 6-CMO: BSA
3-Keto-5α-etianic acid
3-Keto-5β-etianic acid
3-Ketoetiocholanic acid
3-Ketoetiocholanic acid methyl ester
11-Ketoetiocholanolone
3-Keto-4-etiocholenic acid
3-Keto-4-etiocholenic acid ethyl ester
3-Keto-4-etiocholenic acid methyl ester
11-Ketoisoandrosterone
6-Ketolithocholic acid
7-Ketolithocholic acid
12-Ketolithocholic acid
12-Ketolithocholic acid acetate, methyl ester
12-Ketolithocholic acid benzoate, methyl ester
11-Ketopregnanolone
11-Ketopregnanolone acetate
7-Ketopregnenolone
6-Ketoprogesterone
11-Ketoprogesterone
11-Ketotestosterone
16-Ketotestosterone
16-Ketotestosterone acetate
11-Ketotigogenin
Lanosterol
Lithocholic acid
Lithocholic acid acetate
Lithocholic acid acetate methyl ester
Medroxyprogesterone
Megestrol acetate
Meprednisone
Mestranol
4-Methoxyestradiol
2-Methoxyestrapentol
4-Methoxyestriol
2-Methoxyestrone
4-Methoxyestrone
2-Methoxyestrone 3-methyl ether
2-Methoxyethynylestradiol
16α-Methyl-17-acetoprogesterone
Methyl-3α-Acetoxycholanate
Methyl-7α-acetoxy-3,12-diketocholanate
Methyl-3α-acetoxy-12α-hydroxycholanate
Methyl-3α-acetoxy-12-ketocholanate
Methylacetoxylithocholate
Methylandrostanediol
Methylandrostanolone
Methylandrostendiol
Methylchenodeoxycholic diacetate
Methylchenodeoxycholate
Methyl cholate
Methyl cholate 3,7-diacetate
6α-Methylhydrocortisone
Methyldehydrocholate
9(11)-Methyl dehydrotestosterone
Methyldeoxycholate
6α-Methyl-11-desoxycortisol
17α-Methyldihydrotestosterone 3-CMO
Methyldihydrotestosterone
Methyl-3α,12α-dihydroxynorcholanate
Methyl-3α,12α-diol diacetoxynorcholanate
6-Methylidiosgenin
6-Methylidiosgenin acetate
6-Methylepoxypregnenolone
7α-Methylestradiol
Methylestradiol 3-methyl ether
1-Methylestrone
7α-Methylestrone
6α-Methyl-17-hydroprogesterone
16α-Methyl-17-hydroprogesterone
Methylhydroxytigogenin
Methylhydroxytigogenin 3-acetate
Methylhyoxycholate
Methyl lithocholate
7α-Methyl-19-nor-testosterone
17α-Methyl-19-nor-testosterone
Methyloxyprogesterone
6α-Methylprednisolone
6α-Methylprednisolone acetate
6α-Methylprednisolone hemisuccinate
6α-Methylprednisolone sodium succinate
16β-Methylprednisone
6-Methylpregnenolone
6-Methylpregnenolone acetate
16α-Methylpregnenolone
16β-Methylpregnenolone
16α-Methylpregnenolone
16α-Methyl substance "S"
16α-Methyl substance "S" acetate
Methyltestosterone
Δ1-Methyltestosterone
17α-Methyl-Δ1-testerone
2-Methyoxyestradiol
2-Methyoxyestradiol 3-methyl ether
Methyl-3β,12α-diacetoxycholanate
Methyl-3β,12α-diacetoxydeoxycholanate
Murocholic acid
α-Muricholic acid

TABLE 2-continued

LIST OF STEROIDS

β-Muricholic acid
Nandrolone
Neocholestene
Nilevar
6-Nitrocholesteryl acetate
6-Nitrocholesteryl benzoate
2-Nitroestradiol
2-Nitroestrone
19-Nor-4-androsten-3,17-dione
19-Nor-4-androsten-17α-ethyl-17β-ol-3-one
19-Nor-4-androsten-17α-ethynyl-17β-ol-3-one
19-Nor-4-androsten-17β-ol-3-one
19-Nor-Androsterone
Nordeoxycholic acid
Nordeoxycholic acid diacetate
Nordeoxycholic acid diacetate, methyl ester
Nordeoxycholic acid methyl ester
Norethandrolone
Norethindrone
19-Nor-4-ethisterone
Norethynodrel
Norgestrel
Norlutin
19-Norprogesterone
19-Nortestosterone
19-Nortestosterone acetate
19-Nortestosterone benzoate
19-Nortestosterone 3-CMO
19-Nortestosterone dichloroacetate
19-Nortestosterone hemisuccinate
19-Nortestosterone propionate
19-Nortestosterone sodium sulfate
Oxandrolone
Oxymetholone
Prednisolone
Prednisolone acetate
Prednisolone 21-carboxylic acid
Prednisolone hemisuccinate
Prednisolone 21-phosphate, disodium salt
Prednisone
Prednisone acetate
Prednisone 21-hemisuccinate Na salt
Pregnanediol
Pregnanediol diacetate
Pregnanedione
Pregnanetriol
Pregnanetriol 3-glucuronide sodium salt
Pregnanetriolone
Pregnanolone
Pregnanolone acetate
Pregnanolone hemisuccinate
4-Pregnen-11β,21-diol-3,20-dione 18-al
Pregnenindiol
Pregnenolone
Pregnenolone acetate
Pregnenolone acetate oxime
Pregnenolone 20-CMO
Pregnenolone glucuronide
Pregnenolone hemisuccinate
Pregnenolone methyl ether
Pregnenolone sodium sulfate
Pregnenolone tosylate
Δ1-Progesterone
Progesterone
Progesterone 3-CMO
Progesterone 3-CMO: BSA
Provera
Reichstein's epi "U"
Reichstein's substance "A"
Reichstein's substance "B"
Reichstein's substance "Dehydro C"
Reichstein's substance"D"
Reichsrein8s substance Epi "E"
Reichstein's substance "E"
Reichstein's substance "Fa"
Reichstein's substance "G"
Reichstein's substance "H"

TABLE 2-continued

LIST OF STEROIDS

Reichstein's substance "J"
Reichstein's substance "K"
Reichstein's substance "L"
Reichstein's substance "M"
Reichstein's substance "N"
Reichstein's substance "O"
Reichstein's substance "P"
Reichstein's substance "Q"
Reichstein's substance "R"
Reichstein's substance "S"
Reichstein's substance "T"
Reichstein's substance "U"
Reichstein's substance "V"
Rockogenin
Sarsasapogenin
Sarsasapogenin acetate
β-Sitosterol
β-Sitosterol acetate
Smilagenin
Smilagenin acetate
Sodium cholate
Sodium dehydrocholate
Sodium glycochenodeoxycholate
Sodium glycocholate
Sodium glycodehydrocholate
Sodium glycodeoxycholate
Sodium glycohyodeoxycholate
Sodium glycolithocholate
Sodium lithocholate
Sodium taurochenodeoxycholate
Sodium taurocholanic acid
Sodium taurocholate
Sodium taurodehydrocholate
Sodium taurodeoxycholate
Sodium taurohyodeoxycholate
Sodium taurolithocholate
Stanolone
Stigmasradienone
Stigmasterol
Stigmasterol acetate
Stilbestrol
Taurochenodeoxycholic acid
Taurochenodeoxycholic acid sodium salt
Taurocholanic acid
Taurocholanic acid sodium salt
Taurocholic acid
Taurocholic acid sodium salt
Taurodehydrocholic acid
Taurodehydrocholic acid sodium salt
Taurodeoxycholic acid
Taurodeoxycholic acid sodium salt
Taurohyodeoxycholic acid
Taurohyodeoxycholic acid sodium salt
Taurolithocholic acid
Taurolithocholic acid sodium salt
Testane
Δ1-Testosterone
Δ1-Testosterone acetate
Δ1-Testosterone benzoate
Δ1-Testosterone 3-CMO
Δ1-Testosterone hemisuccinate
Δ1-Testosterone hexahydrobenzoate
Δ1-Testosterone propionate
Δ1-Testosterone sodium sulfate
Testosterone
Testosterone acetate
Testosterone benzoate
Testosterone 3-CMO
Testosterone 3-CMO: BSA
Testosterone cyclopentylpropionate
Testosterone dichloroacetate
Testosterone enol diacetate
Testosterone 3-ethyleneketal
Testosterone glucuronide
Testosterone glucuronide sodium salt
Testosterone hemisuccinate
Testosterone hemisuccinate: BSA TABLE 2-continued

LIST OF STEROIDS

Testosterone hexahydrobenzoate
Testosterone phosphoric acid
Testosterone potassium sulfate
Testosterone propionate
Testosterone sodium sulfate
Testosterone tosylate
Tertahydro compound "A"
Tertahydro compound "B"
Tertahydro compound "E"
Tertahydro compound "E" acetate
Tetrahydro compound "F"
Tertahydrocortexolone
Tetrahydrocorticosterone
Tetrahydrocortisol
Tetrahydrocortisone
Tetrahydrocortisone acetate
Tetrahydro-11-dehydrocorticosterone
Tetrahydrodesoxycorticosterone
Tetrahydro-11-desoxycortisol
Tertahydro DOC
Tetrahydro hydrocortisone
Tetrahydro substance "Q"
Tetrahydro substance "S"
Tertahydro substance "S" 21-acetate
TH "A"
TH "B"
TH "E"
TH "F"
TH "S"
TH "S"21-acetate
Theelol
Tigogenin
Tigogenin acetate
Transdehydroandrosterone
Transestriol
Triamcinolone
Triamcinolone acetonide
Triamcinolone diacetate
Triendiol
Triketocholanic acid
Urocortisol
Urocortisone
Ursocholanic acid
Ursodeoxycholic acid
Wintersteiner's compound "A"
Wintersteiner's compound "B"
Wintersteiner's compound "D"
Wintersteiner's compound "F"
Wintersteiner's compound "G"

References

1. Cuschieri, A., 1986. Tumors of the breast: an overview, In: *Comprehensive Textbook of Oncology*, Wiliams & Wilkins p.1002 –1009.
2. Anonymous, 1993. Breast Cancer In: *Handbook of U.S. Desease Incidence and Prevalance* Bio. Bus. Int. p.1–15
3. Harris, J. R., Lippman, M. E., Veronesi, U., Willett, W. 1992. Breast cancer. New Engl. J. Med., V 327, p. 319–328
4. Harris, J. R., Lippman, M. E., Veronesi, U., Willett, W. 1992. Breast cancer. New Engl. J. Med., V 327, p.390–398.
5. Harris, J. R., Lippman, M. E., Veronesi, U., Willett, W. 1992. Breast cancer. New Engl. J. Med., V 327, p.473–480.
6. Kaplan, W. D. 1988. Introduction: Current status of tumour imaging In: *Antibodies in Radiodiagnosis and Therapy*, CRC Press p.2–12.
7. Lentle, B. C., Scott, J. R., Schmidt, R. P., Hopper, H. R., and Catz, Z., 1985, Clinical value of direct tumor scintigraphy: a new hypothesis, J. Nucl. Med., V. 26, p. 1215.
8. Wagner, H. N. 1992. Annual meeting highlights: molecules with messages, J. Nucl. Med., 33:8:p.12 N.
9. Davis, M. A. and Jones, A. G. 1976. Comparison of 99mTc-phosphonate and phosphonate agents for skeletal imaging, Semin. Nucl. Med.,6: p19
10. Brady, L. W. and Croll, M. N., 1979. The role of bone scanning in the cancer patient, Skel. Radiol., V 3, p217.
11. Waxman, A. D. 1982. Scintigraphic evaluation of diffuse hepatic disease, Semin. Nucl. Med.,V 12, p 75.
12. Drum, D. E. 1982. Current status of radiocolloid hepatic scintiphotography for space-occupying disease. Semin. Nucl. Med.,V 13, p 64.
13. Ege, G. N., 1976 Internal mammary lymphoscintigraphy. The rationale, technique, interpretation and clinical application: a review based on 848 cases, Radiology, V 118, p.101
14. Grove, R. B., Reba, R. C., Eckelman, W. C., and Goodyear, M., 1974. Clinical evaluation of radiolabelled bleomycin for tumor detection, J. Nucl. Med., V15, p. 386
15. Hoffer, P., 1980. Status of gallium 67 in tumor detection, J. Nucl. Med., V 21 p. 394.
16. Johnston, G. S., 1981. Clinical applications of gallium in oncology, Int.J. Nucl. Med. Biol. V 8, p.249.
17. Silberstein, E, B., 1978. Gallium scanning in inflammatory and neoplastic conditions, Clin. Nucl. Med., V 6, p.63.
18. Hoffer, P., 1978. The utility of gallium-67 tumor imaging: a comment on the final reports of the cooperative study group. J. Nucl. Med., V 19, p. 1082.
19. Strauss, L. G. and Conti, P. S. 1991. The applications of PET in clinical oncology. J. Nucl. Med. V 32,N 4, p. 623–648.
20. Wahl, R. L. 1990. Sequential quantitative FDG/PET assessment of the metastatic response of breast carcinomas to chemotherapy. J. Nucl. Med. V 31, p.746.
21. Sigurdson, E. R. and Cohen, A. M. 1991. Commentary on applications of PET in clinical oncology. J. Nucl. Med. V 32. p. 649.
22. Spicer, J., Duncan, W. P. and Rotert, G. A. 1984. U.S. Pat. No. 4,659,517
23. Hochberg, J. 1984. U.S. Pat. No. 4,465,676
24. Pomper, M. G., VanBrocklin, H.,and Thieme, A. M. 1990. 11$\beta$-methoxy and 16$\alpha$-fluoroestradiols: receptor based imaging agents. J. Med. Chem. 33:3143–3155
25. Katzenellenbogan, J. A., McElvany K. D. et al. 1982. 16$\alpha$-$^{77}$Br-bromo-11$\beta$-methoxyestradiol: a gamma emitting estrogen imaging agent with high uptake and retention in target organs. J Nucl. Med. 23:411–419.
26. Hanson, R. N., Franke, L. A. et al. 1984. Preparation and evaluation of 17$\alpha$-[$^{125}$I]-iodovinyl-11$\beta$-methoxyestradiol as a selective radioligand for tissues containing estrogen receptors: concise communication, J. Nucl. Med. 25:998–1002.
27. Lipman, M. E., Do, H. M. T., and Hochberg, R. B. 1991. Specific estrogen receptor binding and biological effects of 16 $\alpha$-iodoestradiol on human breast cancer cells. Cancer Res. V 41, p.3150–3154.
28. Zielinski, J. E., Larner, J. M., Hoffer, P. B., and Hochberg, R. B. 1989. The synthesis of 11$\beta$-methoxy-(16$\alpha$-$^{123}$I) iodoestradiol and its interaction with estrogen receptor in vivo and in vitro. J. Nucl. Med. V 30, p.209–215.
29. Ryan, J. W., Rotmensch, J., Pan M-L, et al. 1989. Human biodistribution studies of a novel non-steroidal estrogen (I-123-IBHPE) J. Nucl. Med. V 30, p.883.
30. DeSombre, E. R., Hughes A., Shafii, B. et al. 1992. Estrogen receptor directed radiotoxicity with Auger-electron-emitting nuclides: 17 $\alpha$($^{123}$I)-11$\beta$-methoxtestradiol and CHO-ER cells. In: *Biophysical aspects of Auger Process*. AIP Press p.352–371.

31. McLaughlin, W. H., Milius, R. A., Pillai, K. M., and Blumenthal R. D. 1989. Cytotoxicity of receptor mediated 16α-($^{125}$I) iodoestradiol in cultured MCF-7 human breast cancer cells. J. Natl. Cancer Inst. V 81, p.437–440.
32. DiZio, J. P., Anderson, C. J. et al.1992. Technetium- and rhenium-labelled progestins: synthesis, receptor binding and in vivo distribution of an 11β-substituted progestrin labelled with technetium-99m and rhenium-186. J. Nucl. Med. 33:558–569.
33. Hansen, J. 1975. U.S. Pat. No. 3,927,193
34. Goldenberg, M. D., DeLand, F., Kim, F. 1978. Use of radiolabelled antibodies to carcinoembryonic antigen for the detection and localization of diverse cancers by external photoscanning. N Engl J Med, 298:1384–1388.
35. Kohler, G. and Milstein, C. 1975. Continuous culture of fused cells secreting antibodies of predefined specificity. Nature, 256:495–497.
36. Neal, C. E., Baker, M. R., and Texter, J. H. 1992. Prostate imaging with antibodies. Appl. Radiology, 21:39–46.
37. Wynant, G. E., Murphy, G. P., and Horoszewicz, J. S. 1991. Immunoscintigraphy of prostatic cancer: preliminary results with $^{111}$In-labelled monoclonal antibody 7E11-C5.3 (CYT-356). Prostate, 18:229–241.
38. Horoszewicz, J. S. U.S. Pat. No. 5,162,504
39. Wright, G. L. and Starling, J. J. U.S. Pat. No. 5,153,118.
40. Goldenberg, D. M., DeLand F. H., and Benett, S. J. 1983. Radioimmunodetection of prostatic cancer. In vivo use of radioactive antibodies against prostatic acid phosphatase for diagnosis and detection of prostatic cancer by nuclear imaging. J Amer Med Assoc 2:350–353
41. Wang, E. H., Freidman, P. N., and Prices, C. 1989. Cell 57:379–392.
42. Lamki, L. M., Buzdar, A. M. et al. 1991. Indium-111-labelled B72.3 monoclonal antibody in the detection and staging of breast cancer: a phase 1 study. J. Nucl. Med. 32:1326–1332.
43. Khaw, B. A., Bailes, J. ., Schieder, S. L., Lancaster, J., Powers, J., Strauss, H. W., Lasher, J. C., and McGuire, W. L. 1988. Human breast tumor imaging using $^{111}$In labelled monoclonal antibody: athymic mouse model. Eur. J. Nucl. Med. V.14,p.362–366.
44. Colcher, D., P. Horan, Nuti, M. et al. 1981. A spectrum of monoclonal antibodies reactive with human mammary tumor cells. Proc. Natl. Acad. Sci. V 78, p. 3199–3203.
45. Rainsbury, R. M., Westwood, J. H., Coombes, R. C., Neville, A. M., McCready, V. R., and Gazet, J. C. 1983. Location of metastastic breast carcinoma by a monoclonal antibody chelate labelled with indium-111. Lancet V 1, p. 934–938.
46. Larson, S. M. 1981. Monoclonal antibodies for diagnosis and therapy. Univ. Wash. Med. V 8, p. 22–28.
47. Zalutsky, M. R. 1988. Antibody-mediated radiotherapy: future prospects. In: *Antibodies in Radiodiagnosis and Therapy.* CRC Press p.213–235.
48. Goldenberg, D. M. 1988. Targeting of cancer with radiolabelled antibodies. Arch. Pathol. Lab. Med. V 112 p. 580–587.
49. Elias, D. J., L. E. Kline, R. O. Dillman, R. M. Trim 1990. Treatment of human B-Lymphoma xenografts in nude mice with adriamycin-immunoconjugates prepared using an acid sensitive linker. Antibody Immunoconj. and Radiophrm. V 3, p.60.
50. Sivolapenko, C. Moreno, J. Corvalan, W. Smith, A. Ritter and A. Epenetos 1990. Redustion of the anti-mouse immunoglobulin response using a bispecific monoclonal antibody complexed to vinblastine. Antibody Immunoconj. and Radiophrm. V 3, p.61.
51. Hertel, A., Donnerstag, B., L. Schulte, A. Noujaim, et al. 1992. Therapeutic effects of anti-idiotypic HAMA after immunoscintigraphy in ovarian cancer patients. Eur. J. Nucl. Med., V. 19, p. 608
52. King, D. J., Mountain, J. R., Adair, R. J., Owens, R. J. et al. 1992. Tumor localization of engineered antibody fragments Antibody Immunoconj. and Radiophrm. V 5, p.159–170.
53. Colcher, D., Bird, R., Roselli, M., et al. 1990. In vivo tumor targeting of a recombinant single-chain antigen-binding protein. J. Nat. Cancer Inst. V. 82, p. 1191–1197.
54. Borrebaeck, C. A. 1992. Antibody Engineering: A practical guide. W. H. Freeman and Company.
55. Joiris, E., Bastin B., and Thornback, J. R. 1991. A new method for labelling of monoclonal antibodies and their fragments with $^{99m}$Technetium. Nucl. Med. Biol. V. 18,p. 353–356.
56. Diamandis, EP, YU, H and Sutherland DJA. Detection of prostate specific antigen immunoreactivity in breast tumors. Breast Cancer Res Treat (in press) (1994).
57. Yu, H and Diamandis EP., Ultrasensitive Time-resolved immunof luometric assay of prostate specific antigen in serum and preliminary clinical studies. Clin. Chem. 1993; 99:2108–14.
58. Monne M, Croce C, Yu H, Diamandis EP. Molecular characterization of prostate-specific antigen in breast tissue. Unpublished data.
59. Hsu SM, Rains L, Fanger H. Use of avidin-biotin-peroxidase (ABC) in immunoperoxidase techniques. J. Histochem Cytochem 1981; 29:577–80.
60. Martin, E. W., Mojzisik, C. M., Hinkle, G. H eyt al, (1988) Radioimmunoguided surgery using monoclonal antibody, Am. J. Surgery 156:386–92.

Although preferred embodiments of the invention are described herein in detail, it will be understood by those skilled in the art that variations may be made thereto without departing from the spirit of the invention or the scope of the appended claims.

What is claimed is:

1. An in vivo method for treating endocrine cancer in non-prostatic tissue of a patient comprising:
   injecting the patient having endocrine cancer in non-prostatic tissue with biological binding units which bind to PSA produced by non-prostatic tissue of the patient.

2. A method of claim 1, wherein the biological binding units are injected on a repeated basis to assist the development of antiidiotypic antibodies by the patient.

3. A method of claim 1, wherein the biological binding unit is selected from the group consisting of antibodies, molecular recognition units and peptides.

4. A method of claim 3, wherein the antibodies are selected from the group consisting of polyclonal antibodies, monoclonal antibodies, antibody fragments, antibody constructs, single chain antibodies and bifunctional antibodies.

5. A method of claim 1, wherein the biological binding unit is conjugated with a toxic agent.

6. A method of claim 5, wherein the toxic agent is a radioisotope.

7. A method of claim 6 wherein the radioisotope is selected from the group consisting of $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

8. A method of claim 7, wherein the radioisotope is selected from the group consisting of $^{131}$I, 125I, $^{123}$I, $^{90}$Y, $^{186}$Re, $^{188}$Re, $^{153}$Sm, $^{77}$Br, $^{227}$Ac, $^{211}$At, $^{131}$Ba, $^{77}$Br, $^{32}$P, $^{212}$Bi, $^{166}$Ho, $^{67}$Cu, $^{47}$Sc, and $^{212}$Pb.

9. A method of claim 5, wherein the toxic agent is a therapeutic drug.

10. A method of claim 9, wherein the therapeutic drug is selected from the group consisting of Adriamycin, Chlororambucil, Daunorubicin, Leucovorin, Folinic acid, Methotrexate, Mitomycin C, Neocarzinostatin, Melphalan Vinblastine, Mitocyn, Mechlorethamine, Fluorouracil, Floxuridine, Idarubicin, Doxorubicin, Epirubicin, Cisplatin, Cannustine, Cyclophosphamide, Bleomycin, Vincristine and Cytarabine.

11. A method of claim 5, wherein the toxic agent is a toxin.

12. A method of claim 11, wherein the toxin is selected from the group consisting of diptheria toxin, ricin toxin, Monensin, Verrucarin A, Abrin, Vinca alkaloids, Tricothecenes, and Pseudomonas exotoxin A.

13. A method in accordance with any one of the preceding claims, further comprising the initial step of injecting a patient with a steroid which induces the cancer cells to produce PSA, said cancer cells having receptors for the injected steroid.

14. A method of claim 13, wherein the steroid is chosen from the classes of steroids selected from the group consisting of glucorticosteroids, mineralocorticosteroids, androgens, antiestrogens and progestin.

* * * * *

UNITED STATES PATENT AND TRADEMARK OFFICE
CERTIFICATE OF CORRECTION

PATENT NO. : 6,274,118 B1  
DATED : August 14, 2001  
INVENTOR(S) : Eleftherios P. Diamandis et al.

It is certified that error appears in the above-identified patent and that said Letters Patent is hereby corrected as shown below:

Title page,
Item [30], Foreign Application Priority Data, "93 14623" has been replaced with -- 93 14623.1 --.
Item [56], References Cited, OTHER PUBLICATIONS, the 6$^{th}$ reference in the second column:
"radioimmunotheapy" has been replaced with -- radioimmunotherapy --.
The 7$^{th}$ reference in the second column:
"Immunotheerapy" has been replaced with -- Immunotherapy --.
The 11$^{th}$ reference in the second column:
"Prdiction" has been replaced with -- Prediction --, "Uisng" has been replaced with -- Using --, and "fo" has been replaced with -- of --.
Item [57], ABSTRACT,
Line 8, "radio" has been replaced with -- radio- --.

Column 28,
Line 65, "$^{117m}$mSn" has been replaced with -- $^{117m}$Sn --.

Column 29,
Line 2, "125I" has been replaced with -- $^{125}$I --.
Line 13, "Cannustine" has been replaced with -- Carmustine --.

Signed and Sealed this

Twenty-fourth Day of December, 2002

JAMES E. ROGAN  
*Director of the United States Patent and Trademark Office*